(12) United States Patent
Snow et al.

(10) Patent No.: US 8,365,726 B2
(45) Date of Patent: Feb. 5, 2013

(54) TUB FOR HUMIDIFIER

(75) Inventors: John Michael Snow, Busselton (AU);
 Simon Robert Cork, Wollstonecraft
 (AU); John Zekic, Quakers Hill (AU);
 Benjamin John Hunter, Castle Hill
 (AU)

(73) Assignee: ResMed Limited, Bella Vista (AU)

( * ) Notice: Subject to any disclaimer, the term of this
 patent is extended or adjusted under 35
 U.S.C. 154(b) by 1039 days.

(21) Appl. No.: 12/134,310

(22) Filed: Jun. 6, 2008

(65) Prior Publication Data

US 2008/0302361 A1 Dec. 11, 2008

Related U.S. Application Data

(60) Provisional application No. 60/942,567, filed on Jun. 7, 2007, provisional application No. 61/039,514, filed on Mar. 26, 2008.

(51) Int. Cl.
 *A61M 16/00* (2006.01)
(52) U.S. Cl. ......... 128/203.26; 128/200.24; 128/203.17; 128/203.16; 128/203.27; 128/202.27; 403/321; 403/326; 403/330
(58) Field of Classification Search ................... 403/321, 403/326, 330; 128/203.16, 203.17, 203.26, 128/203.27, 200.11, 202.27
 See application file for complete search history.

(56) References Cited

U.S. PATENT DOCUMENTS

| | | | | |
|---|---|---|---|---|
| 3,994,416 | A | * | 11/1976 | Mulligan ....................... 220/840 |
| 4,714,078 | A | | 12/1987 | Paluch |
| 5,135,284 | A | * | 8/1992 | Crum ....................... 297/440.15 |
| 6,435,180 | B1 | * | 8/2002 | Hewson et al. .......... 128/204.18 |
| 6,527,309 | B1 | * | 3/2003 | Gaydos et al. ................. 292/128 |
| 6,935,337 | B2 | * | 8/2005 | Virr et al. ................. 128/203.16 |
| 7,111,624 | B2 | | 9/2006 | Thudor et al. |
| 2007/0210462 | A1 | | 9/2007 | Felty et al. |
| 2008/0072900 | A1 | | 3/2008 | Kenyon et al. |
| 2008/0105257 | A1 | | 5/2008 | Klasek et al. |

FOREIGN PATENT DOCUMENTS

| | | |
|---|---|---|
| DE | 299 09 611 U1 | 10/1999 |
| GB | 2 293 325 A | 3/1996 |
| WO | WO-2004112873 A * | 12/2004 |
| WO | WO 2008/056993 A2 | 5/2008 |

* cited by examiner

*Primary Examiner* — Lynne Anderson
*Assistant Examiner* — Bradley Philips
(74) *Attorney, Agent, or Firm* — Nixon & Vanderhye P.C.

(57) ABSTRACT

A humidifier includes a tub. The tub includes a base plate; a tub base; a seal between the base plate and the tub base; and a latch mechanism that connects the base plate to the tub base so that the base plate is engaged with the seal. The latch mechanism may include an overcenter latch pivotably attached to the tub base and latch tabs formed on the base plate, the overcenter latch engaging the latch tabs in the connected position to connect the base plate to the tub base. The latch mechanism may alternatively include resilient tabs on the tub base, the resilient tabs elastically biasing the base plate toward the tub base upon connection of the base plate to the tub base. The resilient tabs may include tamper evident projections that indicate that the base plate has been disconnected from the tub base. The base plate may be stainless steel and be formed by stamping. The base plate may include a stamped ring. The humidifier further includes a tub lid configured to cover the tub to form a water container. A cradle receives the water container. A hinged lid on the cradle is pivotable between an open position permitting insertion of the water container into the cradle and a closed position covering the inserted water container. A heating element contacts the base plate when the water container is inserted into the cradle. The humidifier is connectable to a flow generator of a CPAP device.

32 Claims, 25 Drawing Sheets

TUB FOR HUMIDIFIER

CROSS REFERENCE TO RELATED APPLICATION

This application claims priority to U.S. Applications 60/942,567, filed Jun. 7, 2007, and 61/039,514, filed Mar. 26, 2008, the entire contents of both being incorporated herein by reference.

FIELD OF THE INVENTION

The present invention relates to a tub for a humidifier. The present invention also relates to a humidifier for a breathable gas supply apparatus, and particularly but not exclusively, to such apparatus for use in Continuous Positive Airway Pressure (CPAP) treatment of conditions such as Obstructive Sleep Apnea (OSA) and other respiratory disorders and diseases such as emphysema. Although the present invention is described herein in its application to CPAP treatment apparatus, it should be appreciated that the features of the present invention will have application to other fields of application, such as a mechanical ventilation and assisted respiration.

BACKGROUND OF THE INVENTION

CPAP treatment of OSA, a form of Noninvasive Positive Pressure Ventilation (NIPPV), involves the delivery of a pressurized breathable gas, usually air, to a patient's airways using a conduit and a patient interface, for example, a mask. Gas pressure employed for a CPAP typically range from 4 cm $H_2O$ to 28 cm $H_2O$, at flow rates of up to 180 L/min (measured at the patient interface), depending on patient requirements. The pressurized gas acts as a pneumatic splint for the patient's airway, preventing airway collapse, especially during the inspiratory phase of respiration.

CPAP machines including an airflow generator for supplying pressurized air to the patient are known, and over recent years there has been commercial incentive for more compact CPAP machines. However, in seeking to reduce the size of the CPAP machines there has been a trade-off between reduced size on the one hand and reduced performance on the other.

The advantages of incorporating humidification of the air supply to a patient are known, and CPAP machines are known which incorporate humidifying devices, either separately from the flow generator or integrated therewith. An example of an integrated flow generator/humidifier is the ResMed® S7 sold by the assignee of the present application. An example of a humidifier which is separately provided to be connectable to a flow generator is disclosed in U.S. Patent Application Publication 2008/0072900 A1, the entire contents of which are incorporated herein by reference.

It is known to provide a heating unit, such as a heating plate, to a humidifier to increase the amount of water vapor in the flow of breathable gas. Reducing the size of CPAP machines, including humidifiers, has led to a decrease in the size of water containers making it more difficult to provide humidification of the air supply during the entirety of the patient's sleep cycle. The reduction in the size of humidifier tubs results in a decrease in the surface area of the water exposed to the flow of air provided by the flow generator. This creates problems in maintaining a sufficient moisture pickup by the airflow passing through the tub and requires that the flow generator motor run faster, which produces more noise. The integration of humidifiers with flow generators also makes it more difficult to clean the water container of the humidifier.

SUMMARY OF THE INVENTION

One aspect of the invention relates to a humidifier tub that provides enhanced heating for use with a CPAP device.

Another aspect of the invention relates to a humidifier tub that provides increased usable water capacity for use with a CPAP device.

Still another aspect of the invention relates to a humidifier tub for use with a CPAD device that includes a removable base plate to permit cleaning.

According to an embodiment of the invention, a humidifier comprises a tub. The tub comprises a base plate; a tub base; a seal between the base plate and the tub base; and a latch mechanism that connects the base plate to the tub base so that the base plate is engaged with the seal.

According to another embodiment of the present invention, the humidifier comprises a tub lid configured to cover the tub base. The tub and the tub lid form a water container.

According to still another embodiment of the present invention, the humidifier comprises a cradle configured to receive the water container.

According to yet another embodiment of the invention, the cradle is configured to be connected to a flow generator that supplies an air flow to the water container.

According to a further embodiment of the invention, the cradle comprises a hinged lid that is pivotable between an open position permitting insertion of the water container into the cradle and a closed position covering the inserted water container.

According to an even further embodiment, the hinged lid comprises an air outlet pipe configured to communicate with an outlet of the tub lid when the lid is the closed position.

According to another embodiment of the invention, the cradle comprises a heating element configured to contact the base plate when the water container is inserted into the cradle.

According to another embodiment, a CPAP device includes a humidifier according to the invention.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

1.0 Humidifier

Figure 1:
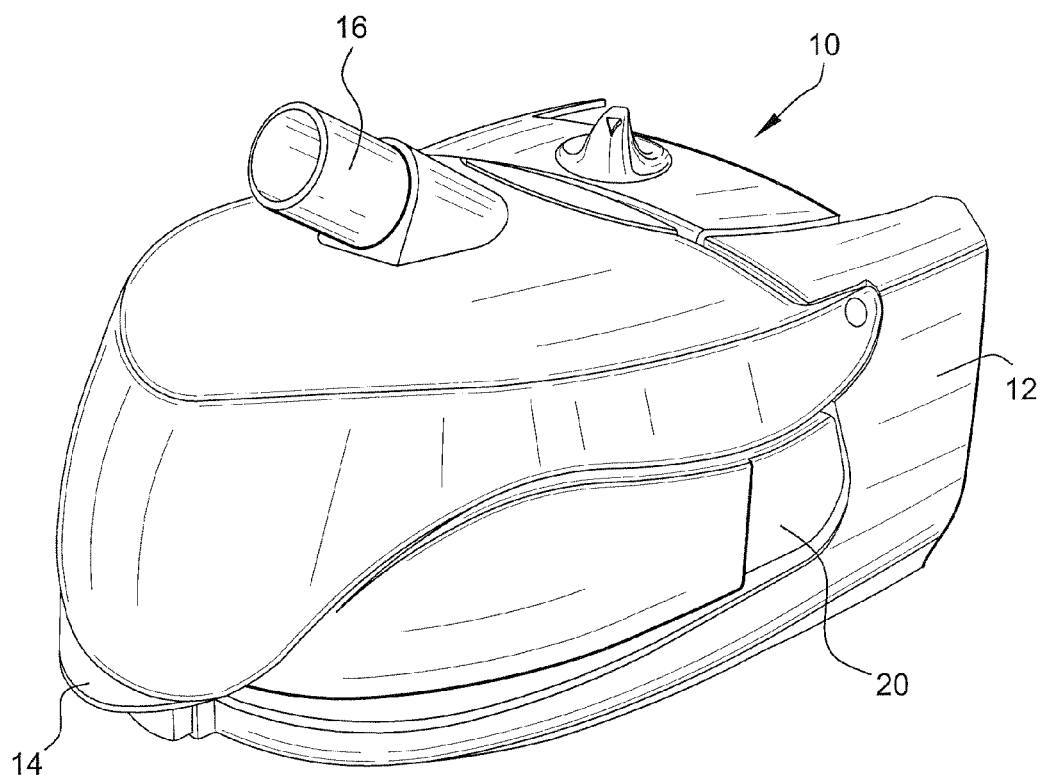
FIG. 1 schematically illustrates a humidifier according to one sample embodiment of the present invention.

Referring to FIG. 1, a humidifier 10 according to an embodiment of the present invention includes a humidifier control base or cradle 12 and a lid 14 hinged to the cradle 12. The hinged lid 14 includes an air outlet pipe 16 which is configured for connection to a hose to deliver a supply of pressurized, breathable gas to a patient via a patient interface, such as a mask. The humidifier 10 includes a water container 20 which is configured to store a supply of water used to humidify the supply of breathable gas. The water container 20 is configured to be inserted, or "dropped," into the cradle 12. The hinged lid 14 is pivotable to an open position (not shown) for insertion of the water container 20 and pivotable to the closed position shown in FIG. 1 to secure the water container 20 in an operable position for connection of the humidifier 10 to a flow generator (not shown). The cradle 12 facilitates the correct assembly of the humidifier 10 with a flow generator. The cradle 12 may include a heating element or plate to heat water within the container 20. Upon insertion of the water container 20 into the cradle 12, the heating element contacts a base plate of the water container 20.

When operating with a hose attached, the lid 14 may be snapped down to create an airtight path, for example using a seal or seals. When the humidifier needs refilling, cleaning, and/or maintenance, the lid may be raised, with the hose still attached, so that the water container is easily accessible. The seal, or seals, of the lid 14 also forms a part of a spill back protection and spitting requirements that protect both the patient and a flow generator. The humidifier is designed to work in a hot and/or humid environment and may be formed of a material that is durable and safe for the patient.

The humidifier is configured to be connected to a flow generator. For example, the humidifier may be connected to a flow generator in a manner similar to that disclosed in WO 2004/112873 A1, the entire contents of which are incorporated by reference herein.

2.0 Tub First Embodiment

Figure 2:
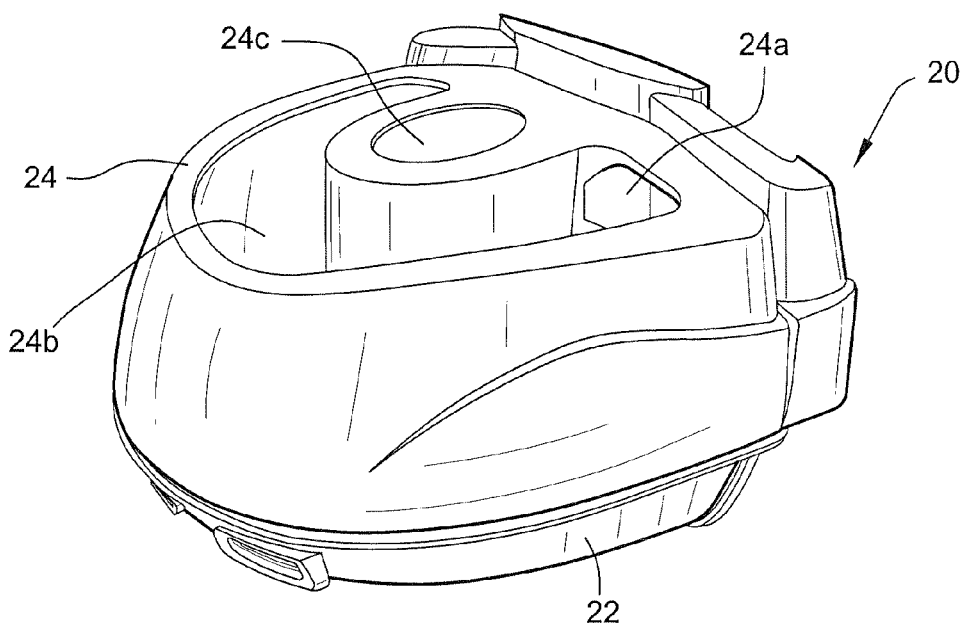
FIG. 2 schematically illustrates a water container of the humidifier of FIG. 1.

As shown in FIG. 2, the water container 20 includes a tub 22 and a tub lid 24. The tub lid 24 includes an air inlet aperture 24*a* that communicates with an air outlet aperture of the flow generator when the humidifier 10 is connected to the flow generator. The tub lid 24 also includes a U-shaped air passage 24*b* and a humidified air outlet 24*c*. The humidified air outlet 24*c* communicates with the air outlet pipe 16 when the hinged lid 14 is in the position shown in FIG. 1 to deliver humidified air to the delivery hose.

Figure 3A:
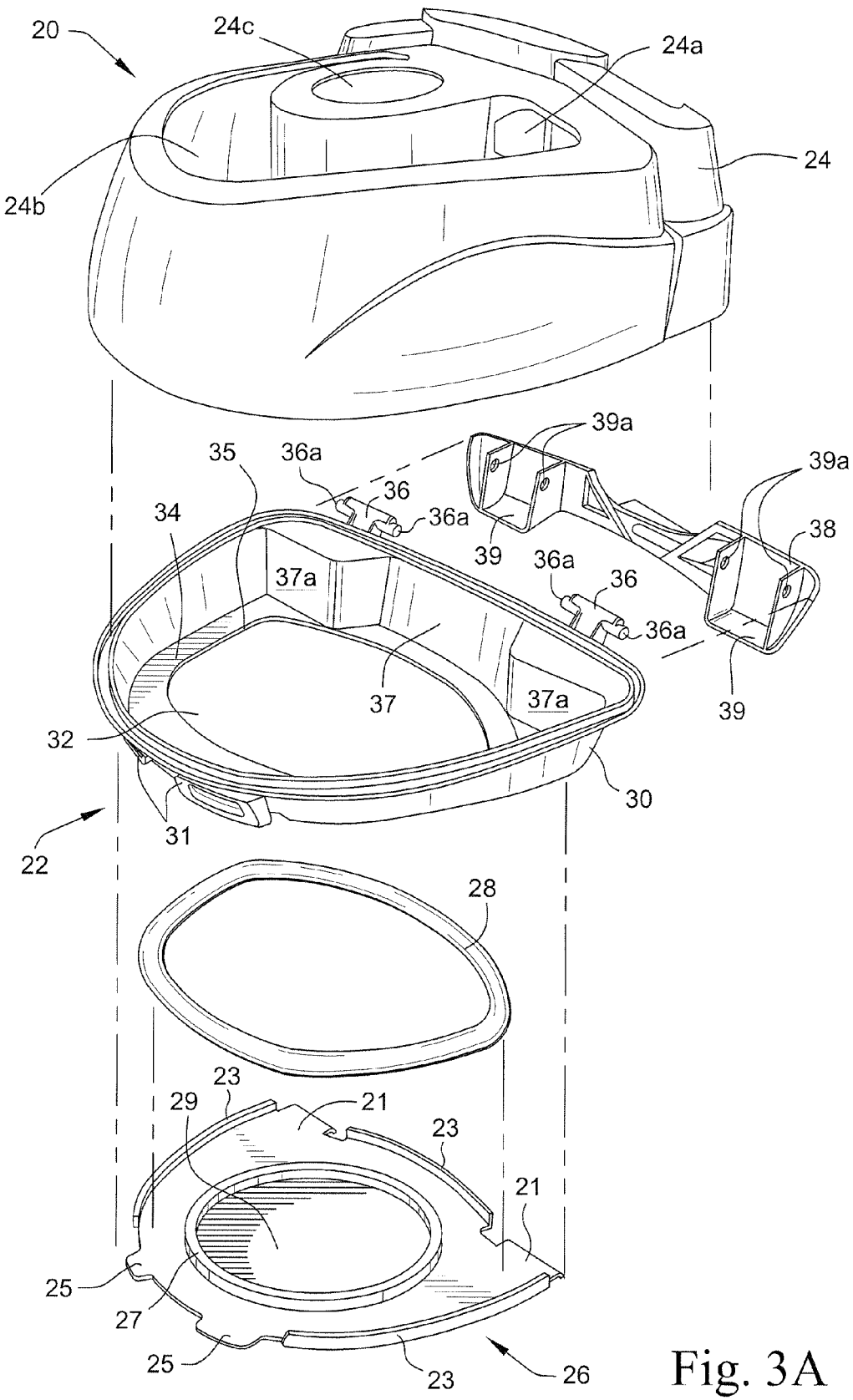
FIG. 3A schematically illustrates an exploded assembly view of the cleanable water container of FIG. 2.

Referring to FIG. 3A, the tub 22 includes a base plate 26 and a tub base 30. The base plate 26 may be formed by stamping, for example, a stainless steel plate. A stamped ring 27 may be formed on the base plate 26 to provide structural rigidity to the base plate 26 so as to provide a flat surface 29. The base plate 26 is also formed with alignment tabs 25 and latch tabs 21.

A face seal 28 is provided between the base plate 26 and the tub base 30. The base plate 26 is attached to the tub base 30, with the face seal 28 therebetween, by inserting the alignment tabs 25 into alignment slots 31 formed in the tub base 30. The portion of the tub base 30 defining the alignment slots 31 may act as feet for the tub 22 to keep the tub 20 level when filling. The alignment slots 31 may be spaced, for example, about 5 mm-15 mm apart, for example about 10 mm. The alignment slots 31 are asymmetrical to ensure correct placement of the base plate 26.

An overcenter latch 38 is connected to the tub base 30 by pivot hinges 36 (FIG. 3D) and the tub 22 is sealed by pivoting the overcenter latch 38 so that latches 39 catch to engage the latch tabs 21 of the base plate 26 to provide a substantially waterproof sealed connection between the tube base 30 and the base plate 26. The latches 39 catch to engage the latch tabs 21 when the overcenter latch 38 is in the engaged position (see FIG. 4) to bias the base plate 26 towards the tub base 30. The face seal 28 is compressed between the base plate 26 and the tub base 30 by the overcenter latch 38 to provide the substantially waterproof seal. As shown in FIG. 4, the overcenter latch 38 may include a textured surface 37 to improve a user's grip on the overcenter latch 38 to permit the overcenter latch 38 to be moved between the engaged and disengaged positions.

The tub base 30 includes a bottom peripheral edge 34 which includes a rim 35 that defines an opening 32 in the tub base 30. The face seal 28 has a shape generally corresponding to the bottom peripheral edge 34 of the tub base 30 and the face seal 28 has a width that is sufficient to permit some misalignment between the tub base 30 and the base plate 26 while still maintaining the substantially waterproof seal. The bottom peripheral edge 34 serves to conceal the edges of the base plate 26, loosely retain the seal 28 during connection of the tub base 30 to the base plate 26, and protect the seal 28 from the edges of the base plate 26 during the connection.

When assembled, the connection of the latch catches 39 and the latch tabs 21 and the insertion of the alignment tabs 25 into the alignment slots 31 define a generally triangular compression region for the face seal 28, which may be, for example, an O-ring. As shown in FIG. 3A, the seal 28 may have a generally D-shaped configuration. It should be appreciated, however, that the seal 28 may have another shape, for example an oval shape.

Figure 3B:
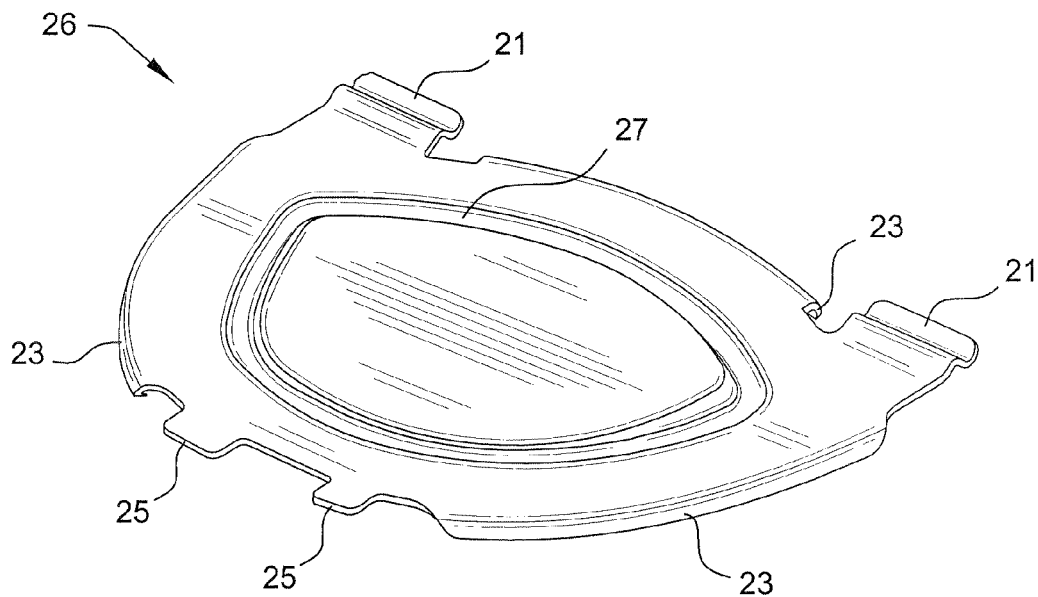
FIG. 3B schematically illustrate a bottom perspective view of a variant of a base plate usable in the assembly of FIG. 3A.

The base plate 26 may also comprise raised edges 23 between the latch tabs 21 and between the latch tabs 21 and the alignment tabs 25. The raised edges 23 add stiffness to the base plate 26 to permit the base plate 26 to resist bending under the stresses induced by the pressure of compressing the seal 28. The stamped ring 27 acts to isolate the contact surface of the base plate 26 from the installation forces and enable the seal pressing process to maintain a flat region. In a variant shown in FIG. 3B, the stamped ring 27 may be formed to match the shape of the seal 28.

The tub base 30 may include done or more 37a provided around a portion of the perimeter of the opening 32 to stiffen the portion of the tub base 30 that will experience high connection forces. The rear portion of the tub base 30 will experience high connection forces when the overcenter latch 38 is connected to the latch tabs 21. The rear corners of the tub base 30 will experience the highest connection forces as the latch catches 39 are connected to the tub base 30 at these locations. The rib 37a acts to prevent deflection of the rear portion of the tub base 30. A central gap 37 may be provided in the rib 37a to enable water to drain onto the base plate 26 and ensure that all of the water in the tub 22 is usable.

Figure 3C:
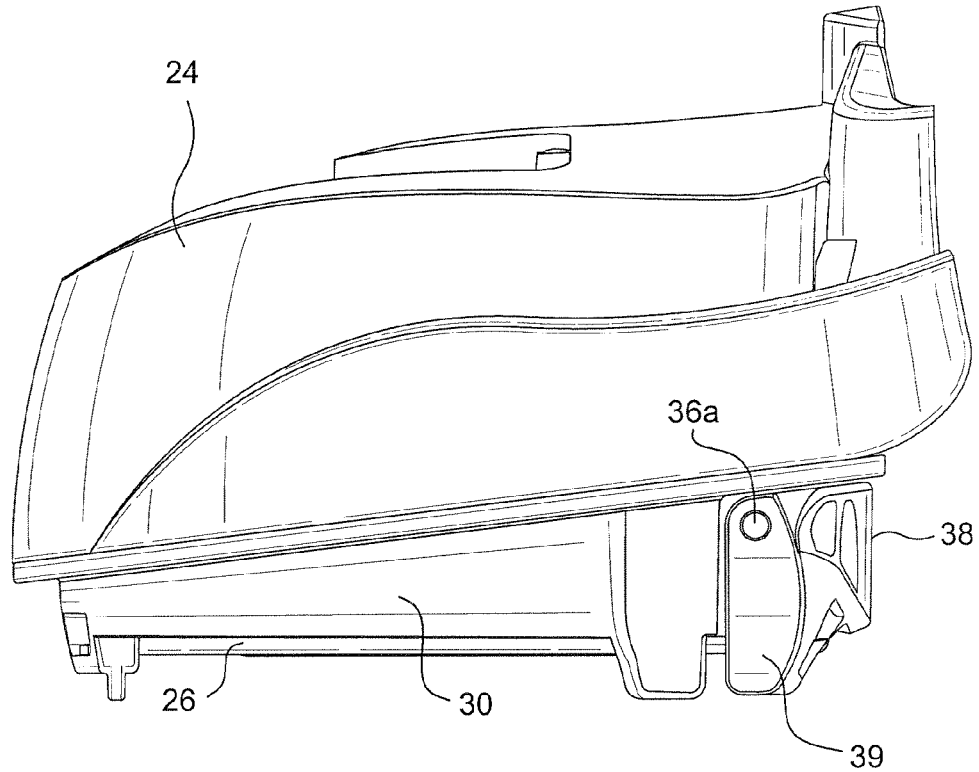
FIG. 3C schematically illustrates a side elevation view of the cleanable water container of the humidifier of FIG. 1.
Figure 3D:
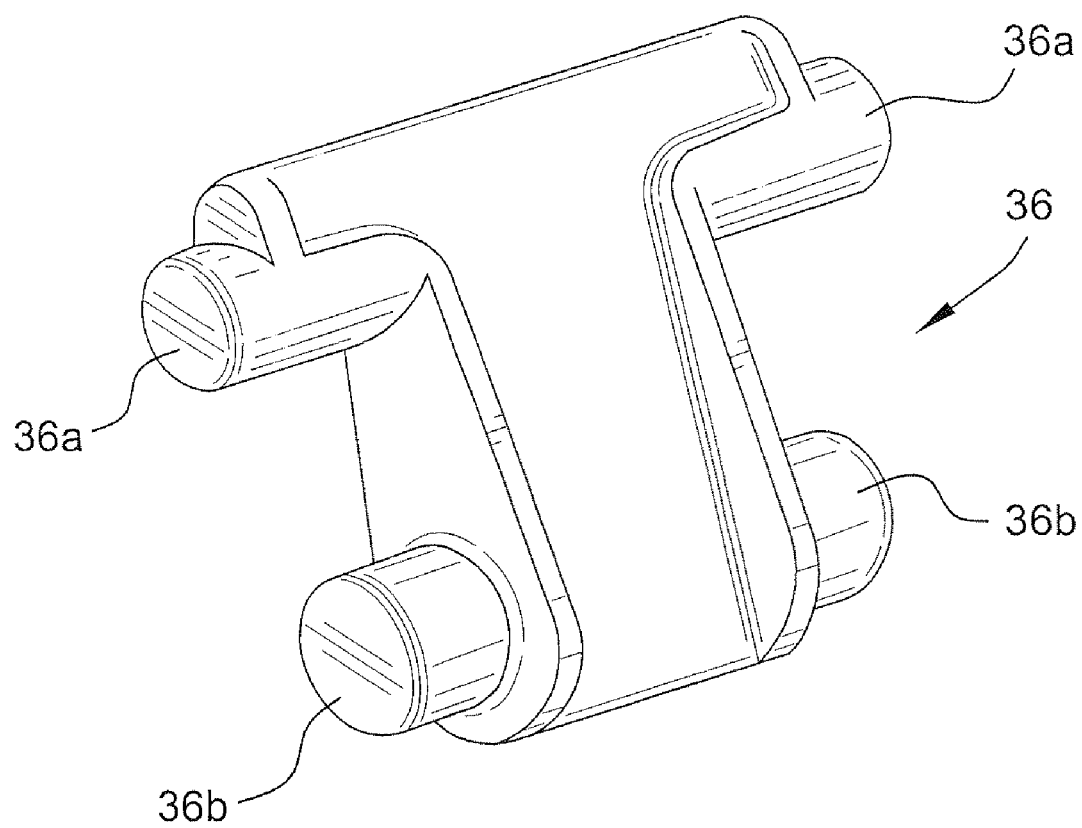
FIG. 3D schematically illustrates a pivot hinge usable with the water container of FIGS. 3A-3C.
Figure 4:
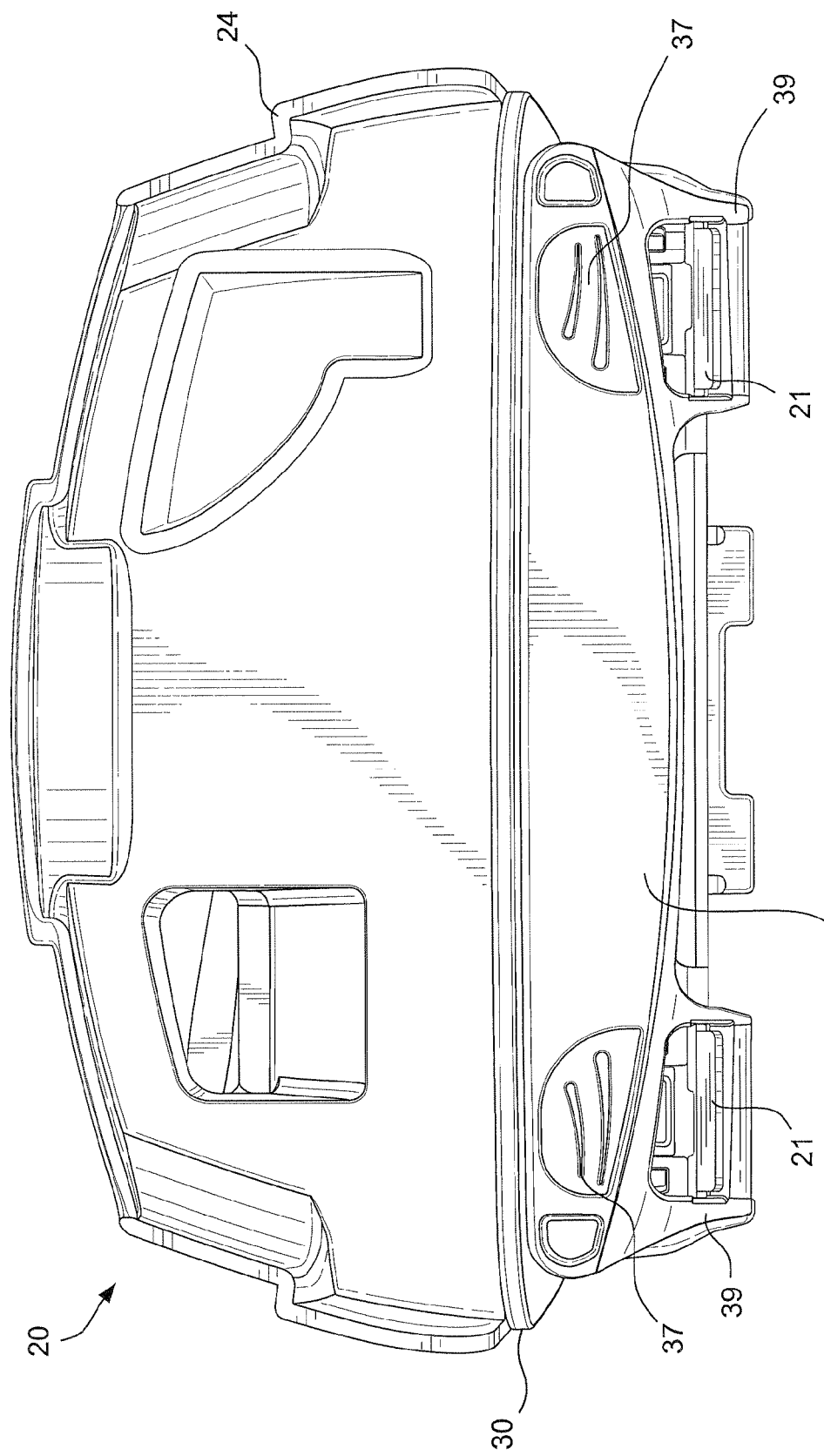
FIG. 4 schematically illustrates a rear elevation view of the cleanable water container of FIGS. 2 and 3A-3D.

Referring to FIGS. 3C and 3D, the pivot hinges 36 are secured to the tub base 30 by pivots 36b of the pivot hinge 36. The rear of the tub base 30 may include four protrusions having holes in each protrusion to accept the pivots 36b of the pivot hinges 36. The latch catches 39 include holes or apertures 39a (FIG. 3A) configured to receive respective pivots 36a of the pivot hinge 36.

The overcenter latch 38 forms a part of the user interface for the humidifier tub. The overcenter latch 38 provides the interfaces for opening and closing the overcenter latch 38 and it interfaces with the base plate 26 to produce the compression force on the face seal 28.

2.1 Tub Second Embodiment

Figure 5:
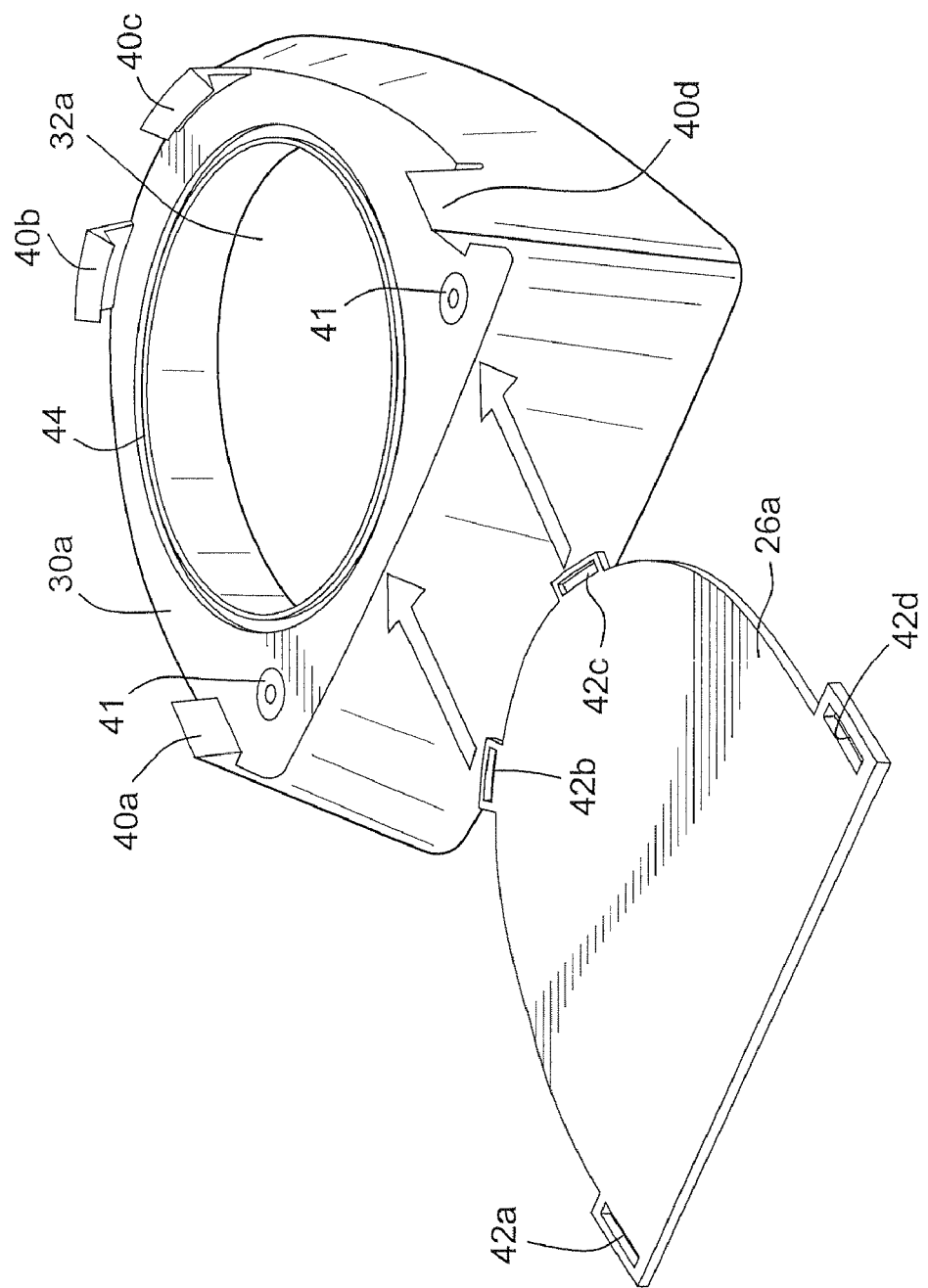
FIGS. 5 and 6 schematically illustrate a humidifier tub according to another sample embodiment of the present invention.
Figure 6:
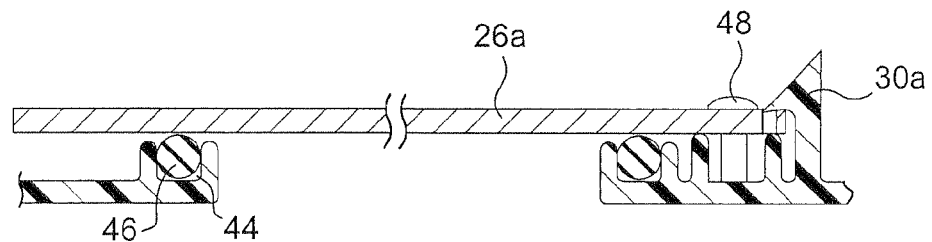

Referring to FIGS. 5 and 6, according to another embodiment of the present invention, the tub base 30a may include a plurality of locking tabs 40a-40d. The base plate 26a is inserted over the opening 32a in the tub base 30a as shown by the arrows in FIG. 5. It should also be appreciated that the base plate 26a may be inserted over the opening in a direction perpendicular to the direction shown by the arrows. The locking tabs 40a-40d are resilient and are received in locking slots 42a-42d provided in the base plate 26a in a snap-in manner. A groove 44 surrounds the periphery of the opening 32a in the tub base for receipt of a seal 46, such as an O-ring. The tub base 30a may also include fastener fittings 41 for receipt of fasteners 48. It should be appreciated that the fasteners 48 may be any releasable fastener.

2.2 Tub Third Embodiment

Figure 7:
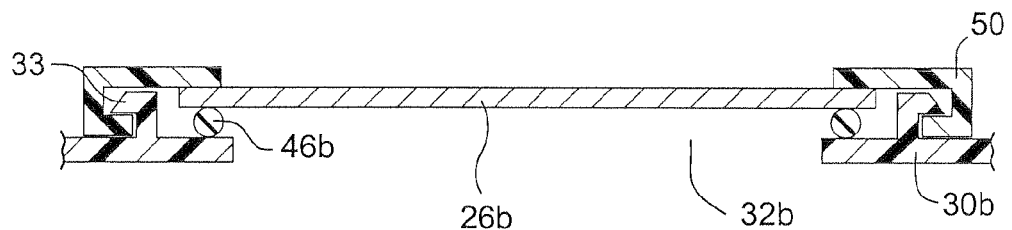
FIG. 7 schematically illustrates a humidifier tub according to another sample embodiment of the invention.

Referring to FIG. 7, the base plate 26b may be releasably secured to the tub base 30b by tabs 33 formed on the tub base 30b and snap rings 50. The base plate 26b is placed over the opening 32b in the tub base 30b in contact with the seal 46b. The snap rings 50 are then placed over the base plate 26b and in engagement with the tabs 33 to secure the base plate 26b between the snap rings 50 and the seal 46b. The tabs 33 are resiliently deformed by insertion of the snap rings 50 so that the snap rings 50 are secured in the position shown in FIG. 7.

2.3 Tub Fourth Embodiment

Figure 8:
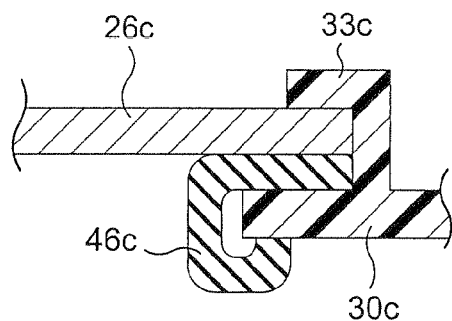
FIG. 8 schematically illustrates a humidifier tub according to another sample embodiment of the present invention.

According to another embodiment shown in FIG. 8, the base plate 26c may be secured to the tub base 30c by tabs 33c and a seal 46c. The seal 46c may be secured to the tub base 30c so as to secure the base plate 26c between the seal 46c and the tabs 33c.

2.4 Tub Fifth Embodiment

Figure 9:
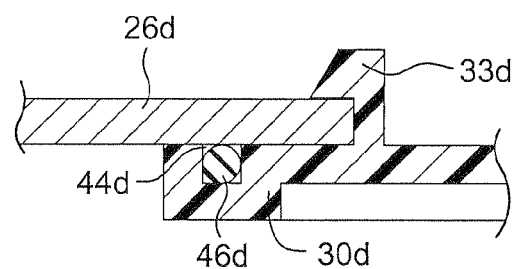
FIG. 9 schematically illustrates a humidifier tub according to another sample embodiment of the present invention.

According to another embodiment shown in FIG. 9, the base plate 26d may be secured to the tub base 30d by tabs 33d. A groove 44d is provided in the tub base 30d and the seal (e.g., O-ring) 46d is provided in the groove 44d to seal the connection between the base plate 26d and the tub base 30d.

2.5 Tub Sixth Embodiment

Figure 10:
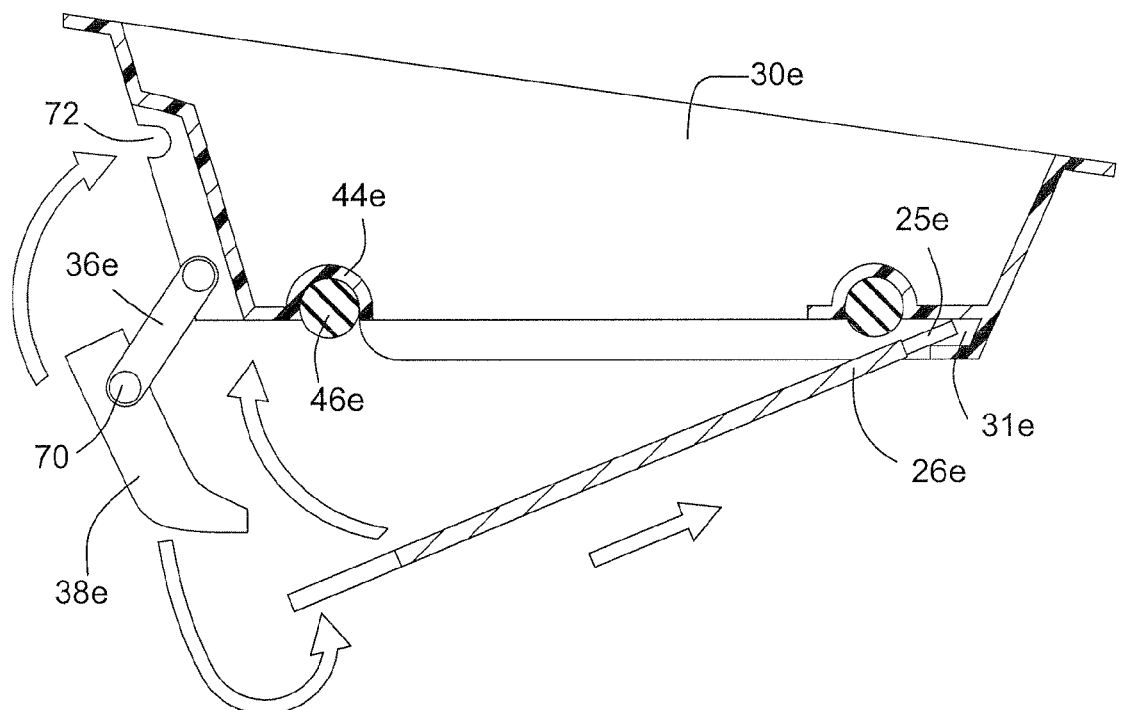
FIG. 10 schematically illustrates a humidifier tub according to another sample embodiment of the present invention.

Referring to FIG. 10, the tub base 30e includes a groove 44e to accommodate a seal 46e, such as an O-ring. Alignment tabs 25e of the base plate 26e are inserted into alignment slots 31e in the tub base 30e and the opposite end of the base plate 26e is then pivoted toward the tub base 30e. An overcenter latch 38e connected to the tub base 30e by a pivot hinge 36e. After the alignment tabs 25e of the base plate 26e are inserted into the alignment slots 31e, the opposite end of the base plate 26e is pivoted toward the tub base 30e. A first end of the overcenter latch 38e is pivoted into engagement with opposite end of the base plate 26e and the second end of the overcenter latch 38e is then pivoted into the assembled condition such that a pin 70 of the pivot hinge 36e is placed in a notch 72 in the tub base 30e.

2.6 Tub Seventh Embodiment

Figure 11:
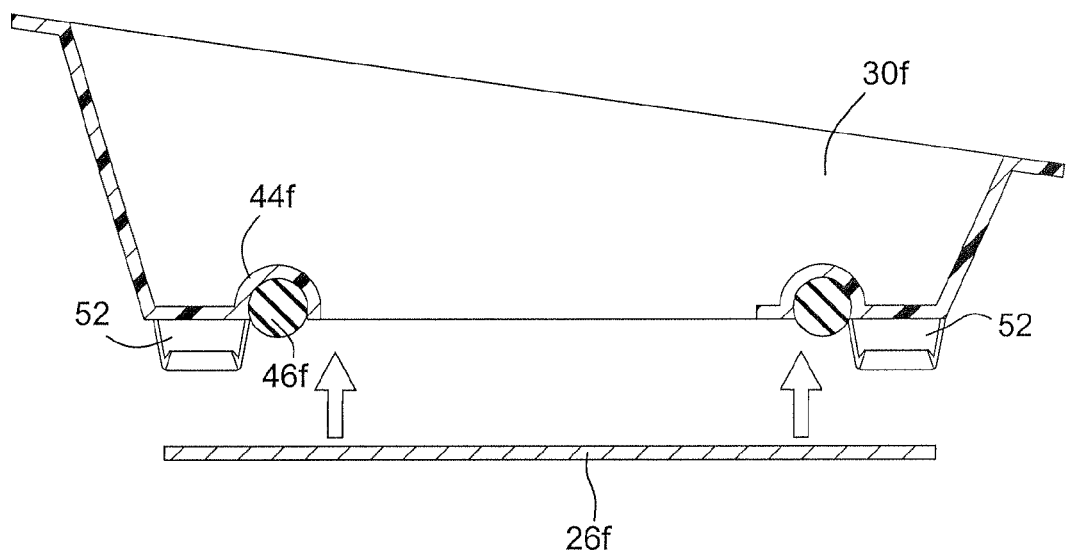
FIGS. 11 and 12 schematically illustrate a humidifier tub according to another sample embodiment of the present invention and FIG. 12A illustrates an additional variant.
Figure 12:
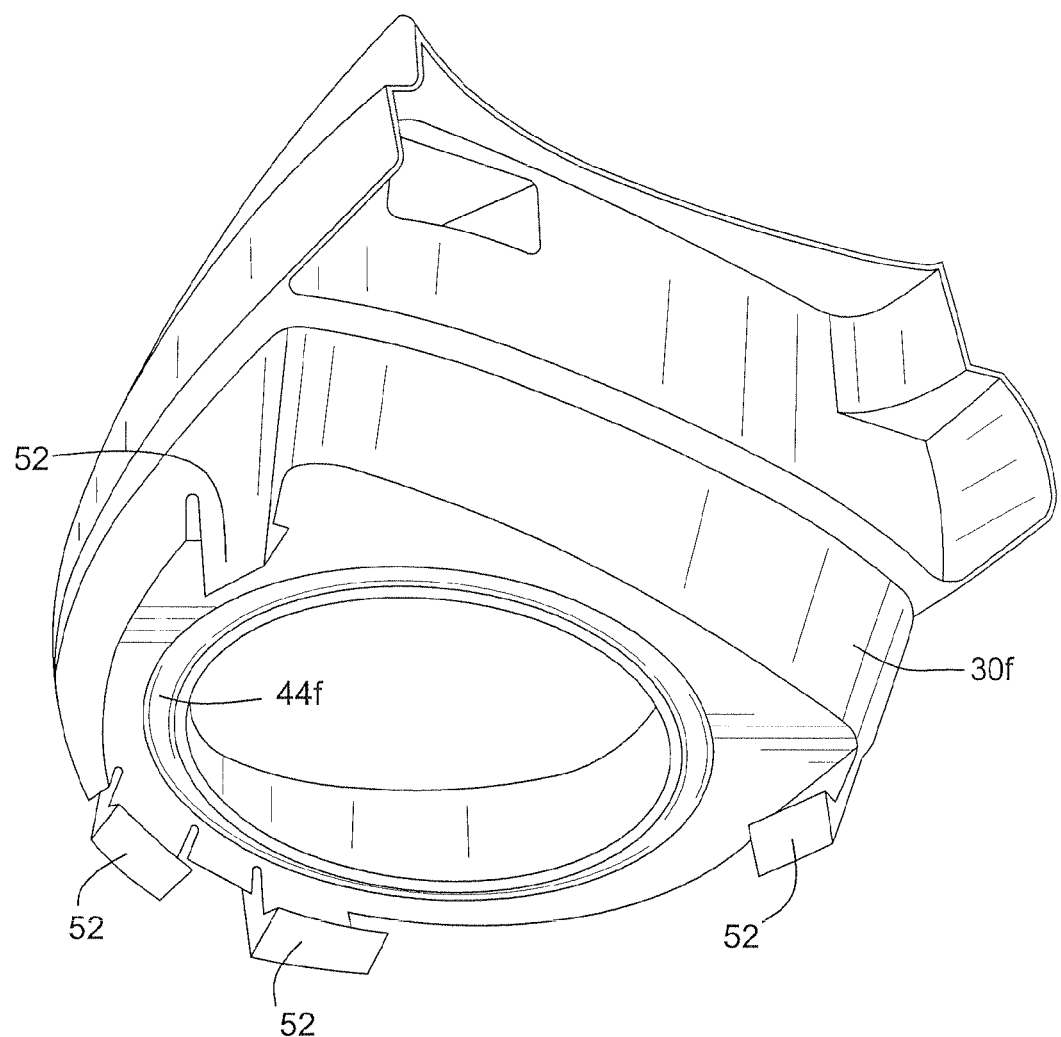
Figure 12A:
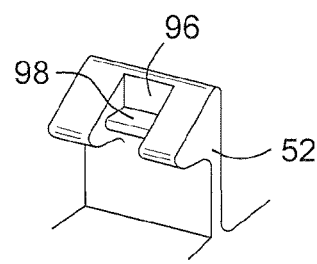

Referring to FIGS. 11 and 12, the tub base 30f includes a groove 44f for accommodating a seal 46f. Tabs 52 are provided on the tub base 30f and the base plate 26f is assembled to the tub base 30f by inserting the base plate 26f to the tube base 30f in the direction shown by the arrows in FIG. 11. The tabs 52 are resilient and the base plate 26f causes an elastic displacement of the tabs 52 upon insertion. The displaced tabs 52 remain somewhat displaced upon full insertion of the base plate 26f to bias the base plate 26f in contact with the seal 46f. Referring to FIG. 12a, the tabs 52 may include tamper evident projections. The tamper evident projections provide evidence of tampering with the base plate 26f in a situation in which the base plate 26f is designed to be removed only by technician. The tabs have a slot 96 with a fragile rib 98 which would crush if tampered with.

2.7 Tub Eighth Embodiment

Figure 13:
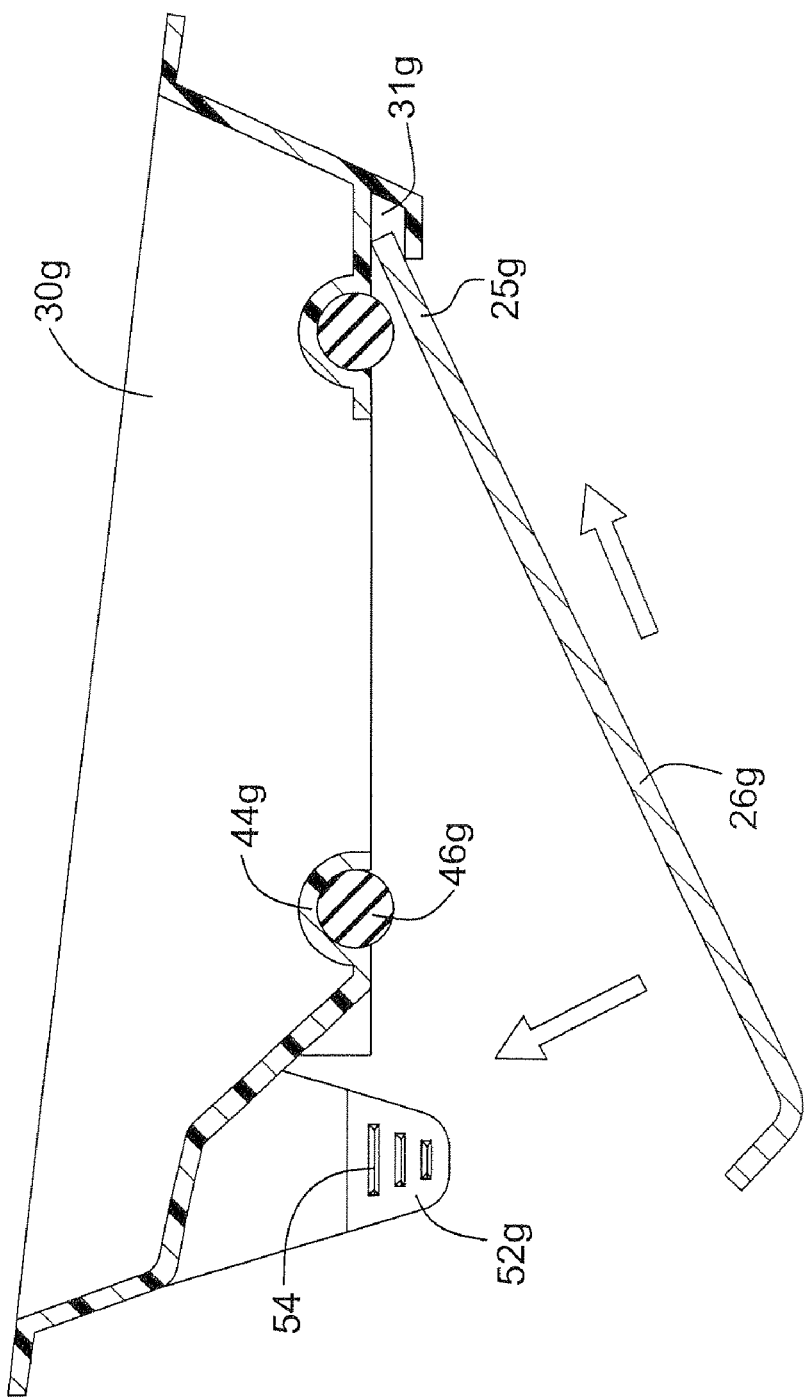
FIGS. 13 and 14 schematically illustrate a humidifier tub according to another sample embodiment of the present invention.
Figure 14:
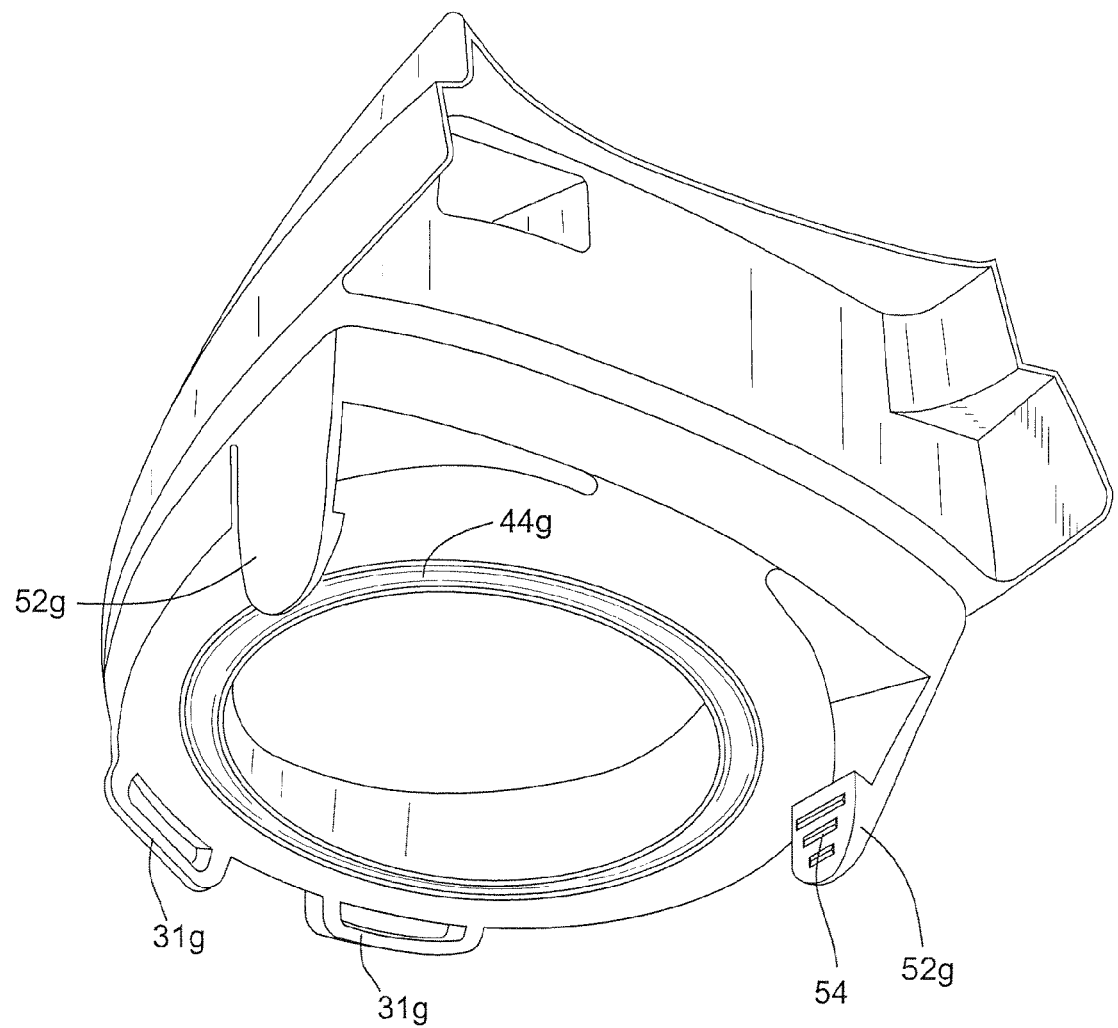

According to another embodiment of the present invention shown in FIGS. 13 and 14, alignment tabs 25g of the base plate 26g are inserted into alignment slots 31g in the tub base 30g. The opposite end of the base plate 26g is then pivoted toward the tub base 30g in the direction shown by the arrow in FIG. 13. The base plate 26g is pivoted into connection with a seal 46g which is accommodated in a recess 44g in the tub base 30g. Resilient tabs 52g are provided for securing the base plate 26g to the tub base 30g. The tabs 52g include textured finger grips 54.

2.8 Tub Ninth Embodiment

Figure 15:
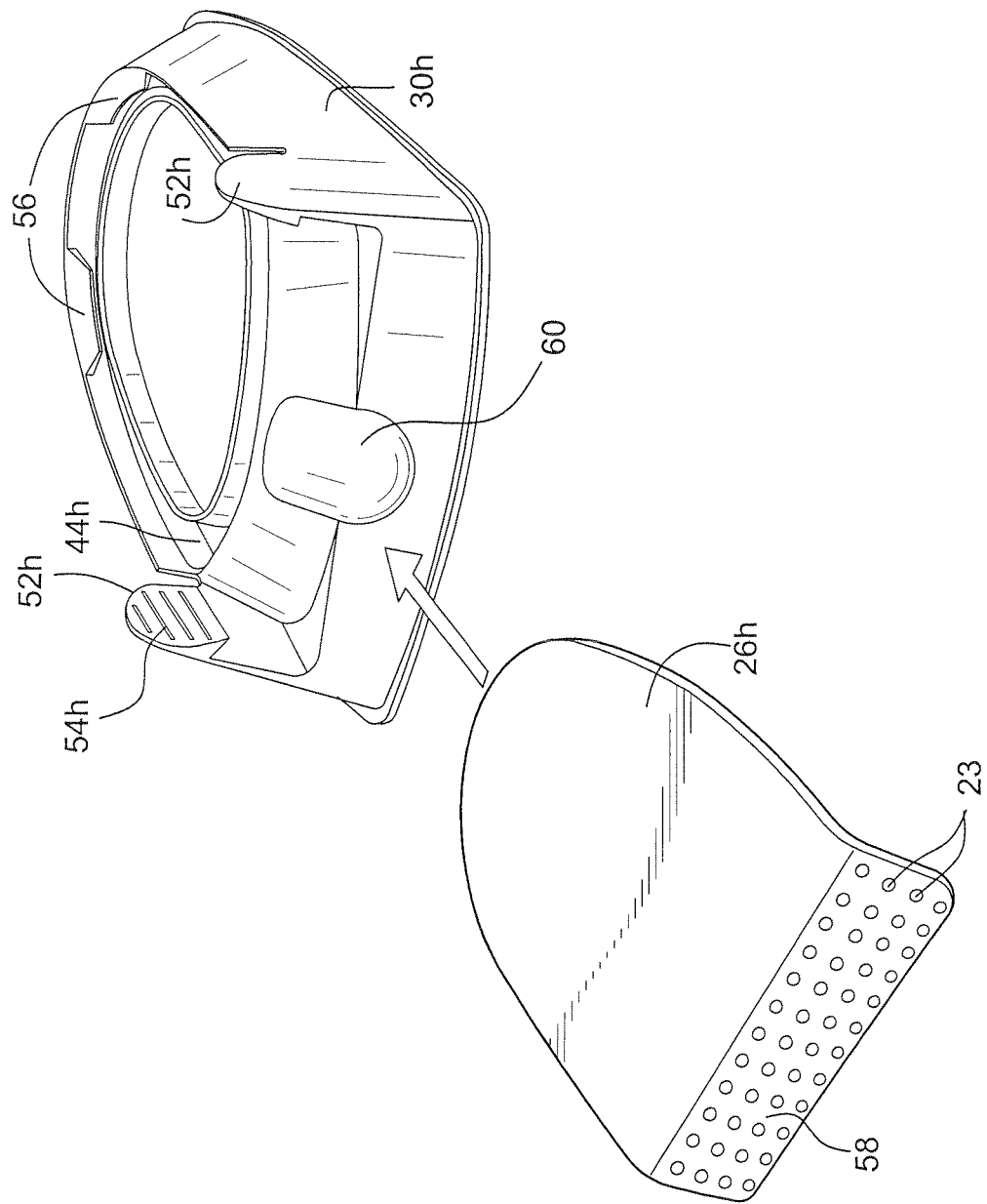
FIGS. 15 and 16 schematically illustrate a humidifier tub according to another sample embodiment of the present invention.
Figure 16:
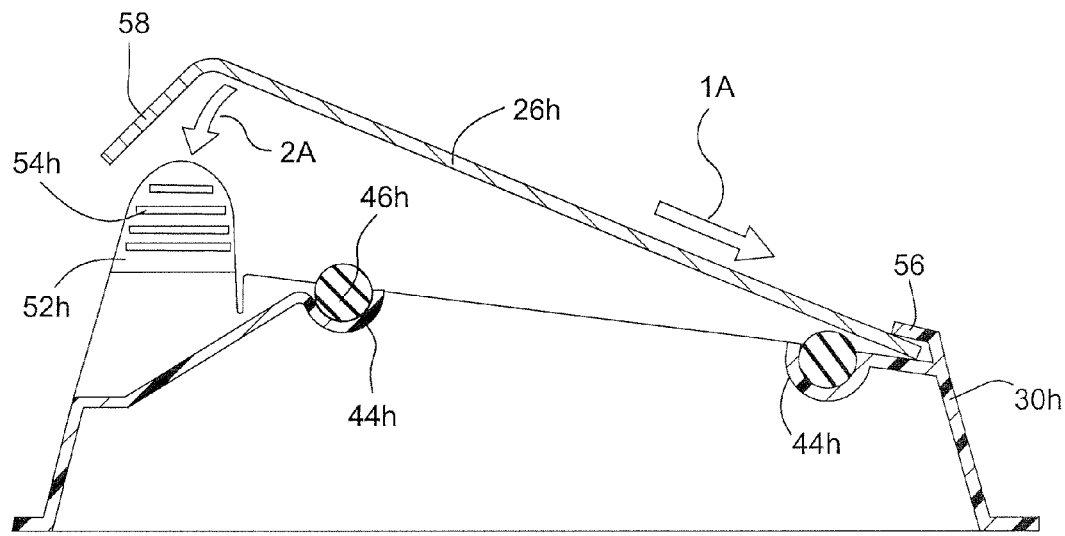

Referring to FIGS. 15 and 16, according to another embodiment of the present invention, the base plate 26h is attached to the tub base 30h in the direction shown by the arrow 1A then 2A in FIG. 16. Lips 56 on the tub base 30h receive the inserted end of the base plate 26h. As shown in FIG. 16, the base plate 26h is then pivoted into engagement with a seal 46h accommodated in groove 44h of the tub base 30h. The base plate 26h includes an inclined second end 58 which is pivoted past resilient tabs 52h which include finger grips 54h. The second end 58 of the base plate 26h may include a textured surface 23 to improve the user's grip on the base plate 26h. As shown in FIG. 15, a depression 60 is formed into the tub base 30h to facilitate insertion of a user's finger upon initial displacement of the base plate 26h to the disassembled position and to permit easier removal of the base plate 26h from the tub base 30h. The base plate 26h may be removed in the direction opposite to the arrow shown in FIG. 15.

2.9 Tub Tenth Embodiment

Figure 17:
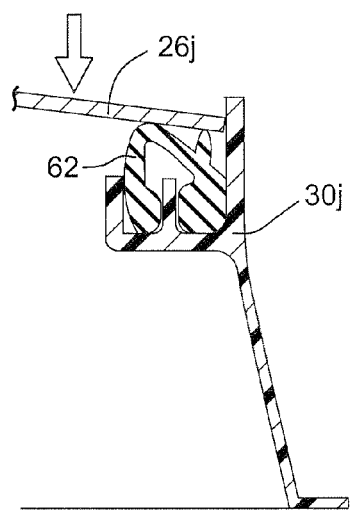
FIG. 17 schematically illustrates a humidifier tub according to another sample embodiment of the present invention.

Referring to FIG. 17, a seal 62 is provided between the base plate 26j and the tub base 30j. The seal 62 acts as a spring to bias the base plate 26j. The seal 62 may be used in any of the embodiments disclosed herein.

2.10 Tub Eleventh Embodiment

Figure 18:
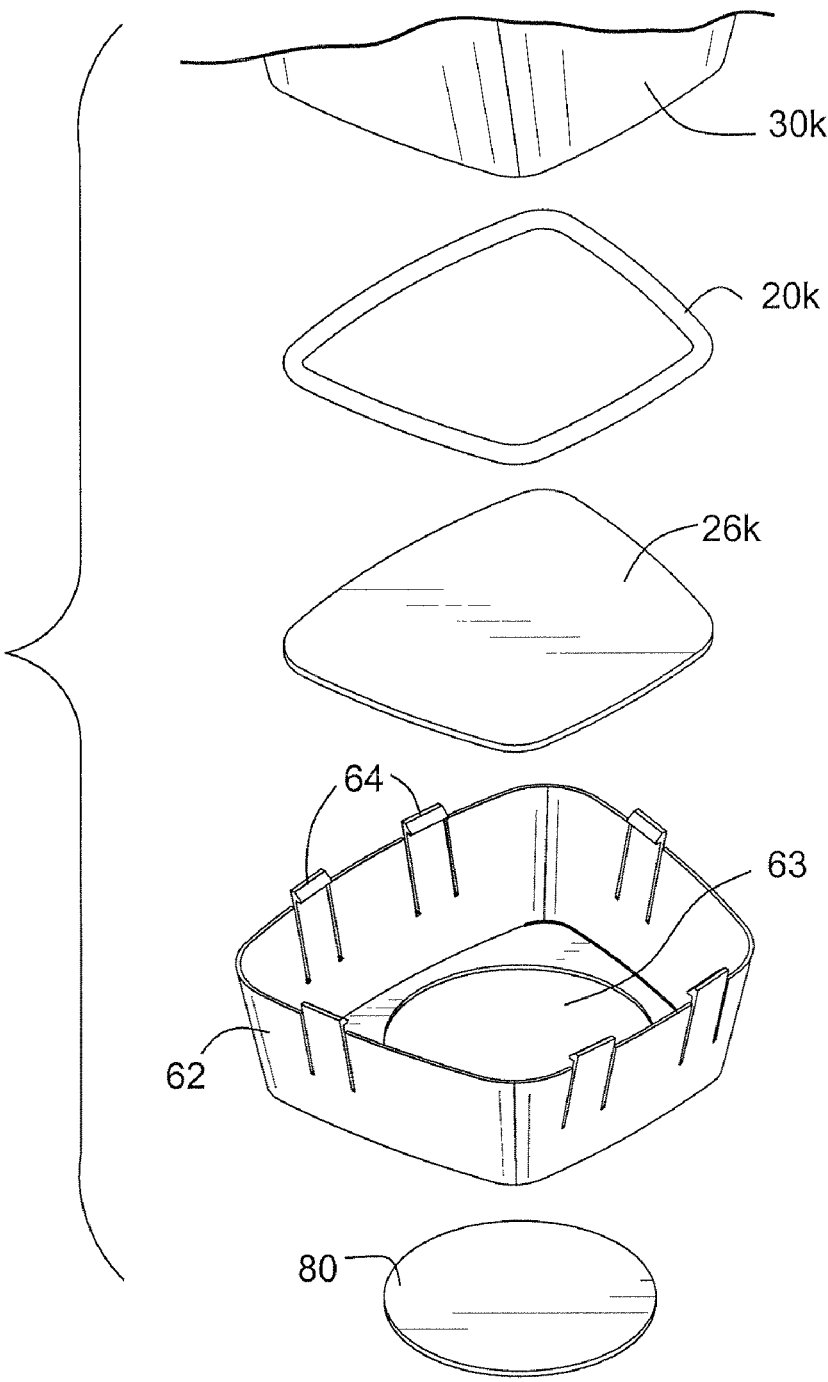
FIGS. 18 and 19 schematically illustrate a humidifier tub according to another sample embodiment of the present invention.
Figure 19:
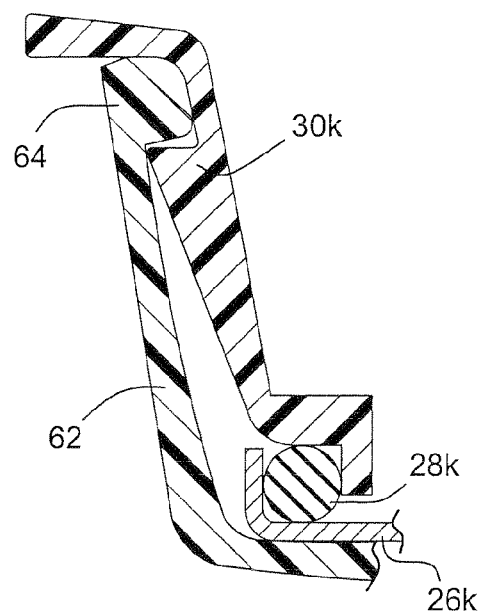
Figure 20:
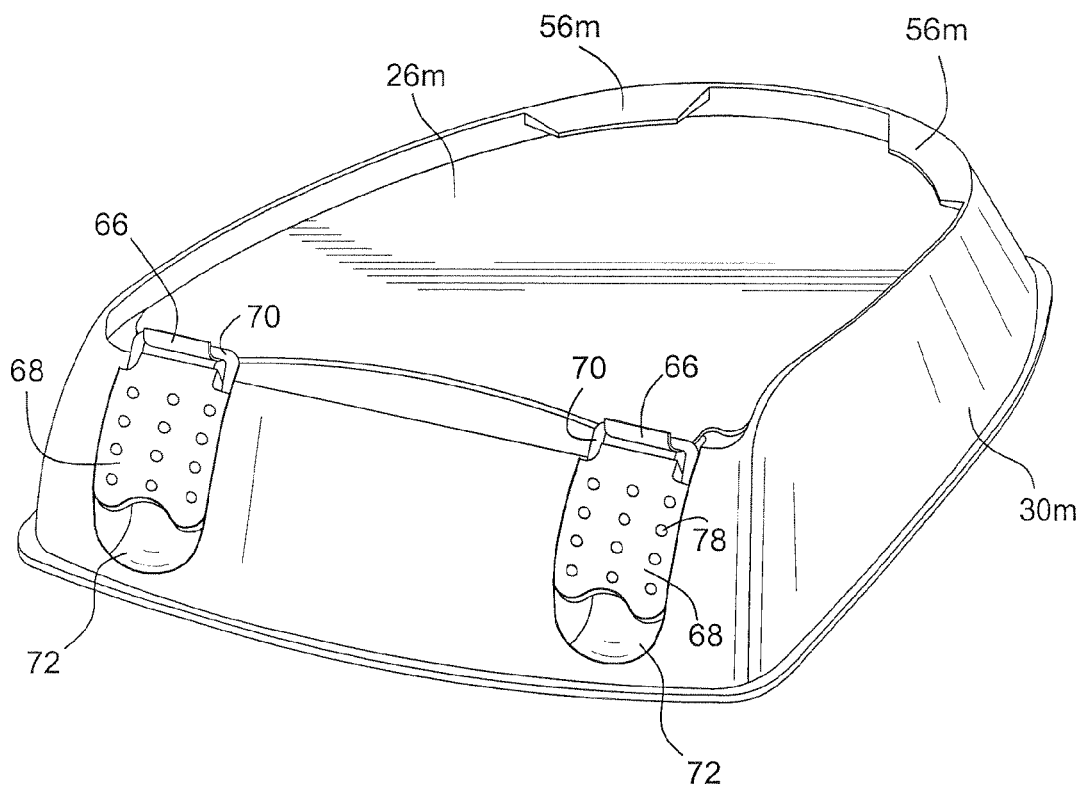
FIGS. 20-23 schematically illustrate a humidifier tub according to another sample embodiment of the present invention.
Figure 21:
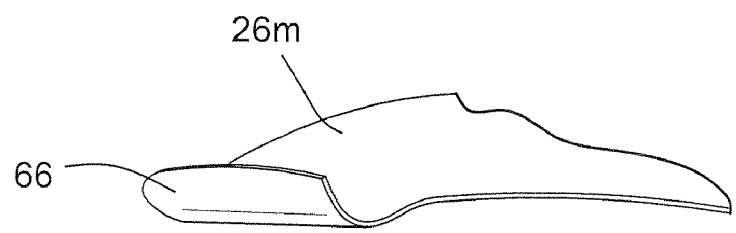
Figure 22:
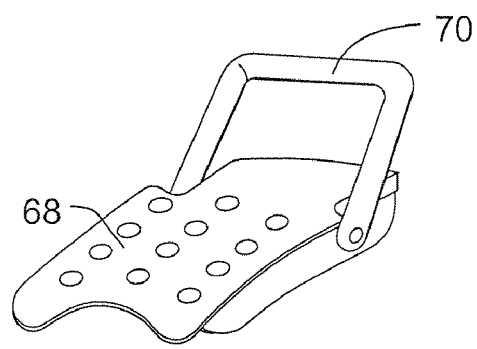
Figure 23:
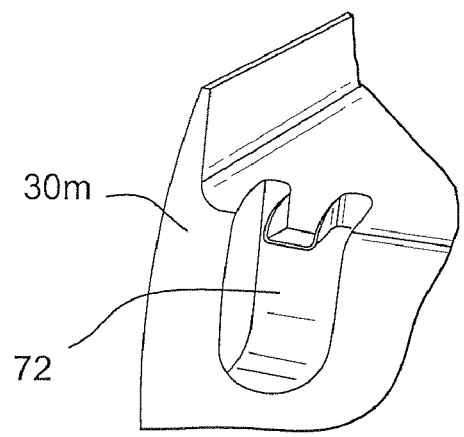

Referring to FIGS. 18 and 19, a base unit 62 includes latches 64 around a top perimeter to lock the tub base 30k into engagement with the seal 28k. The base plate 26k is provided between the base unit 62 and the tub base 30k and the seal 28k is sandwiched between the base plate 26k and the tub base 30k. As shown in FIG. 19, the latches 64 secure the contact between the tub base 30k and the seal 28k and the contact between the seal 28k and the base plate 26k to form a substantially waterproof seal. The base unit 62 includes an opening 63. A heating element or unit 80, such as a ceramic plate, is received in the opening 63 so as to be in contact with the base plate 26k when the tub is assembled in the base unit 62. Contact between the base plate 26k and the heating element 80 is maintained by the engagement of the latches 64 with the tub base 30k. The latches 64 bias the tub base 30k toward the base plate 26k thus biasing the base plate 26k into contact with the heating element 80. The base unit 62 may be provided as an integral part of the casing 12, or separate from the casing.

2.11 Tub Twelfth Embodiment

According to another embodiment of the present invention shown in FIGS. 20-23, a first end of the base plate 26m is inserted into the tub base 30m and held in place by lips 56m. The second, opposite end of the base plate 26m is secured by overcenter cams 68 that engage cam levers 66 provided on the base plate 26m. Each overcenter cam 68 is pivotably attached to the tub base 30m so as to be received in a recess 72 into the tub base 30m. Each overcenter cam 68 includes a linkage 70 which engages the cam lever 66 of the base plate 26m to secure the attachment of the base plate 26m to the tub base 30m. A surface texture 78, such as depressions or projections, may be provided to the overcenter cams 68 that improve a user's grip on the overcenter cams 68.

2.12 Tub Thirteenth Embodiment

Figure 24:
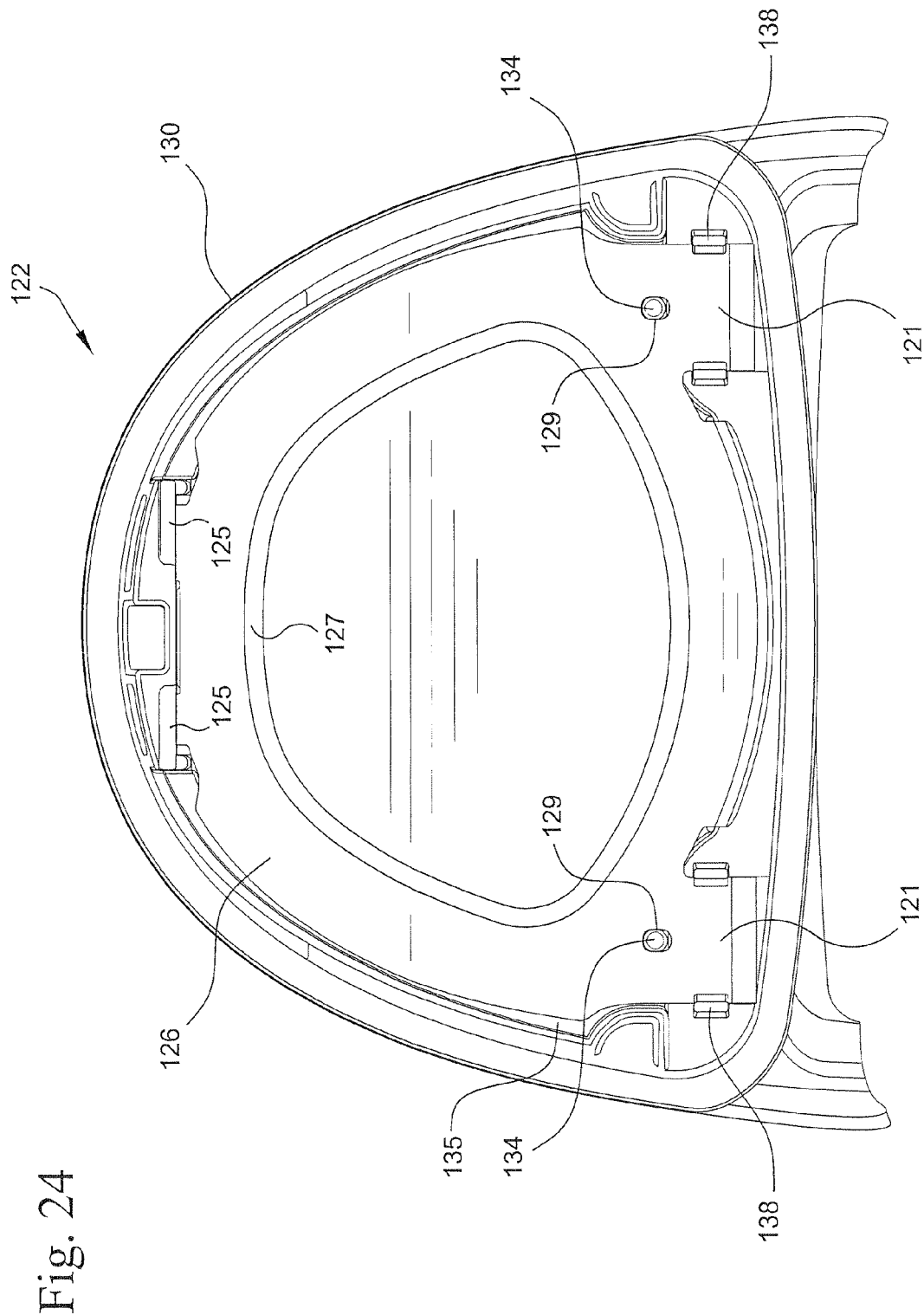
FIGS. 24-26 schematically illustrate a humidifier tub according to another sample embodiment of the present invention.
Figure 25:
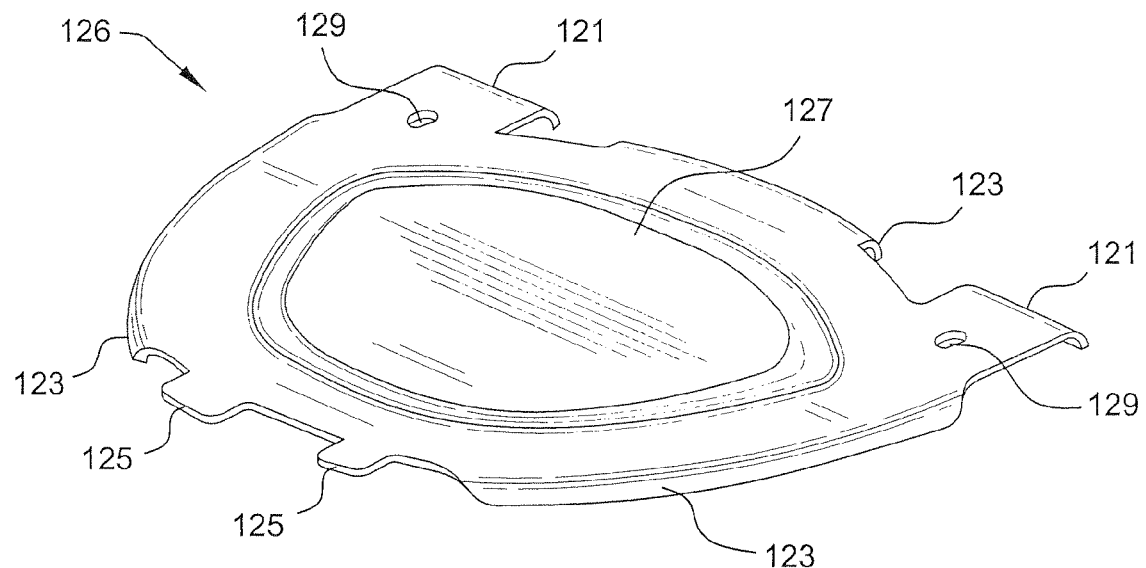
Figure 26:
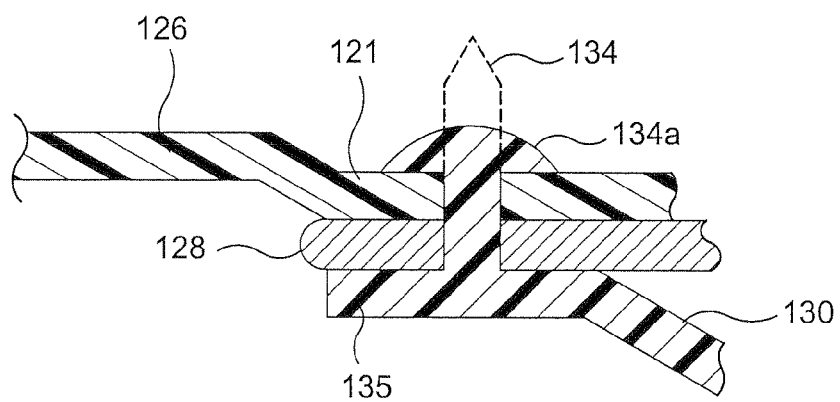
Figure 27:
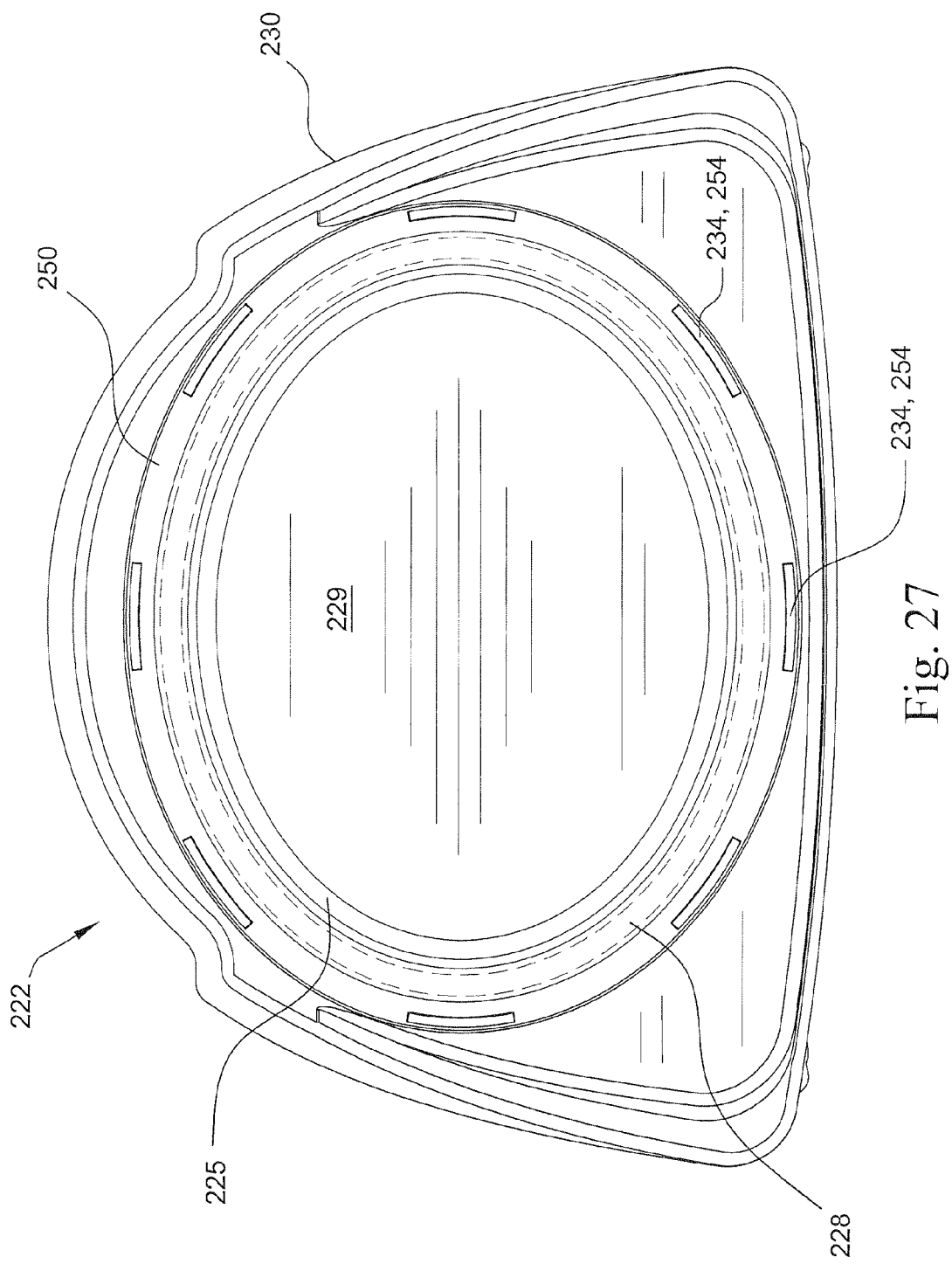
FIGS. 27-32 schematically illustrate a humidifier tub according to another sample embodiment of the invention.

Referring to FIGS. 24-26, another sample embodiment of the humidifier tub 122 may comprise a tub base 130 and a base plate 126. A seal 128 (FIG. 26) is compressed between a bottom peripheral edge 135 of the tub base 130 and the base plate 126 to form a water tight tub 122. The base plate 126 may comprise a stamped ring 127, which may have a shape corresponding to the seal 128.

The base plate 126 may be permanently attached to the tub base 130 by tabs, or snaps, 138 formed in the tub base 130 that engage latch tabs 121 on the base plate 126. The tabs, or snaps, 138 may be similar to the tabs shown, for example, in FIGS. 11-16. The snaps 138 are arranged in sets of two, symmetrical around the center of the tub base 130, and together with alignment tabs 125 of the base plate 126 that are inserted into alignment slots (not shown) of the tub base 130, form a generally triangular compression region for the seal 128.

The snaps 138 grip opposite sides of the latch tabs 121 on the base plate 126 and provide the force for compressing the seal 128 and hold the base plate 126 in position for heat staking. As shown in FIGS. 24-26, the base plate 126 comprises apertures 129 in the latch tabs 121. The tub base 130 further includes heat stakes 134 that extend through the apertures 129 in the latch tabs 121, as shown in FIG. 26. The heat stakes 134 are passed through apertures in the seal 128 and through the apertures 129 in the base plate 126. The top of the heat stake is then melted, for example using a heated probe or an ultrasonic horn, to create a blob of plastic. The dome 134a of the heat stake 134 assists in holding the base plate 126 in position in a permanent manner that is clearly visible.

2.13 Tub Fourteenth Embodiment

Referring to FIGS. 27-32, a humidifier tub 222 according to another sample embodiment comprises a tub base 230 and a base plate 226. The base plate 226 may be formed, for example, as a generally oval stainless steel plate pressed from coil. The base plate 226 comprises a rib 225 that isolates a contact surface 227 from forces that connect the base plate 226 and the tub base 230 and maintain a flat surface 229 of the base plate. A seal 228 is provided on the contact surface 227.

The base plate 226 is connected to the tub base 230 by a snap ring 250. The snap ring 250 includes a contact surface 252. When the tub is assembled, the contact surface 252 engages the bottom of the seal 228 and the top of the seal 228 is engaged by the contact surface 227 of the base plate 226. The seal 228 is compressed between the contact surface 252 of the snap ring 250 and the contact surface 227 of the base plate 226.

Figure 28:
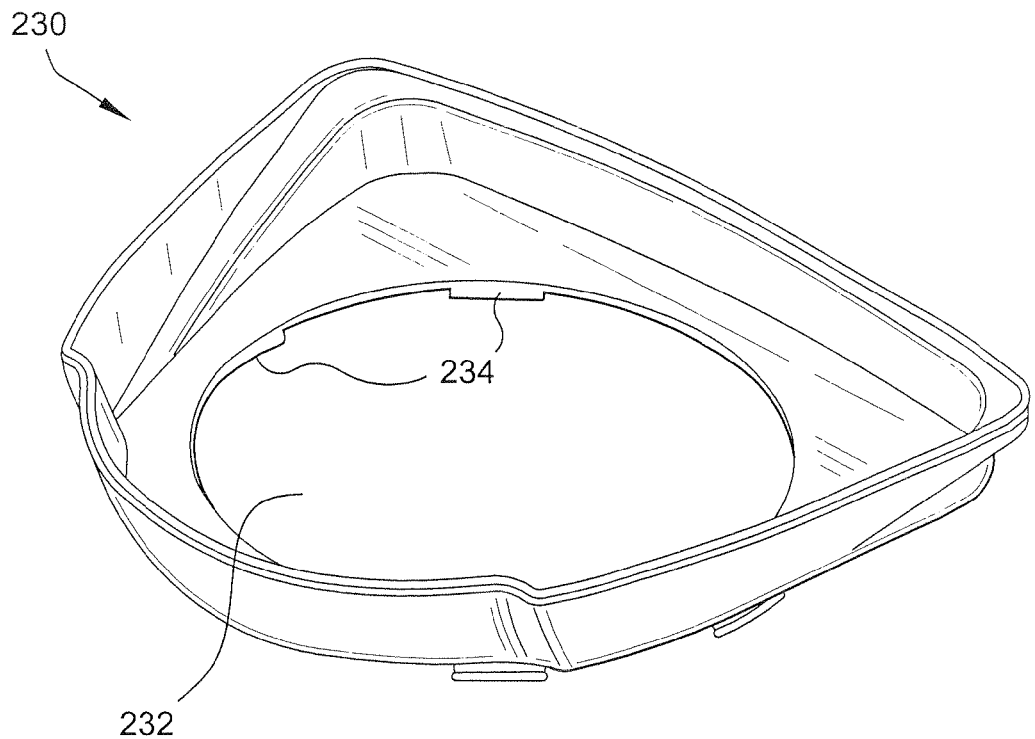
Figure 29:
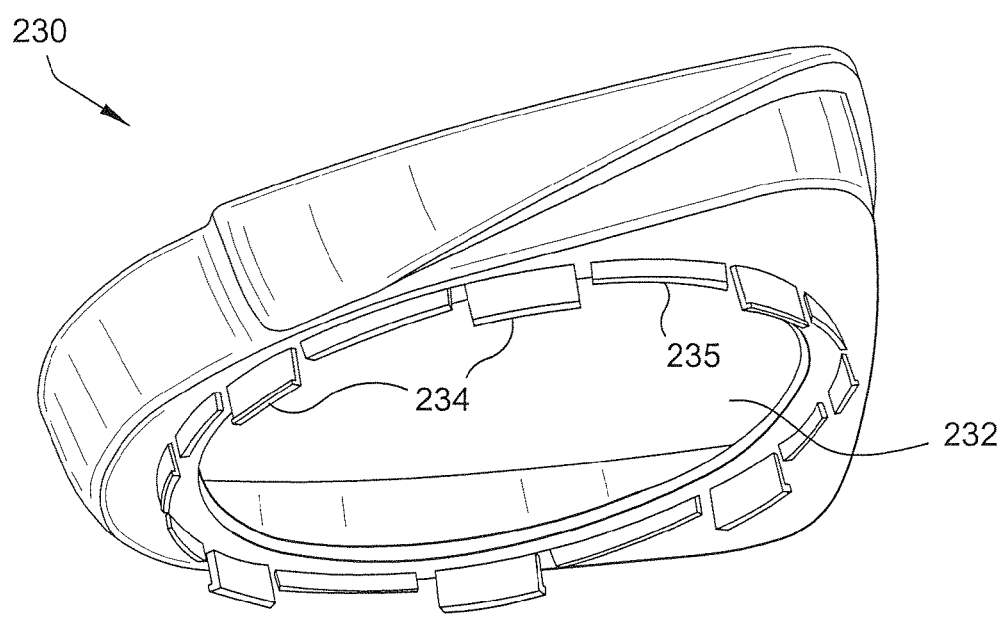
Figure 30:
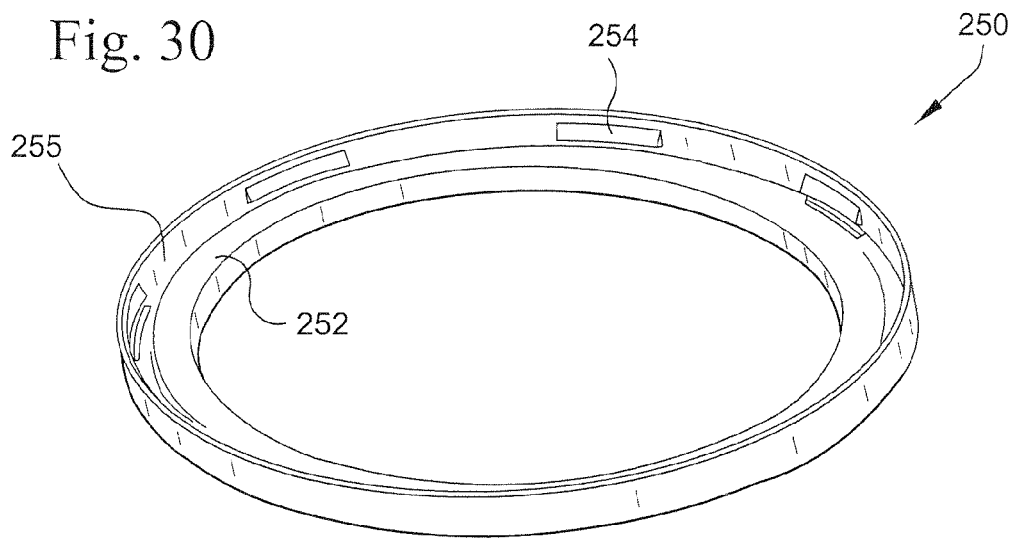
Figure 31:
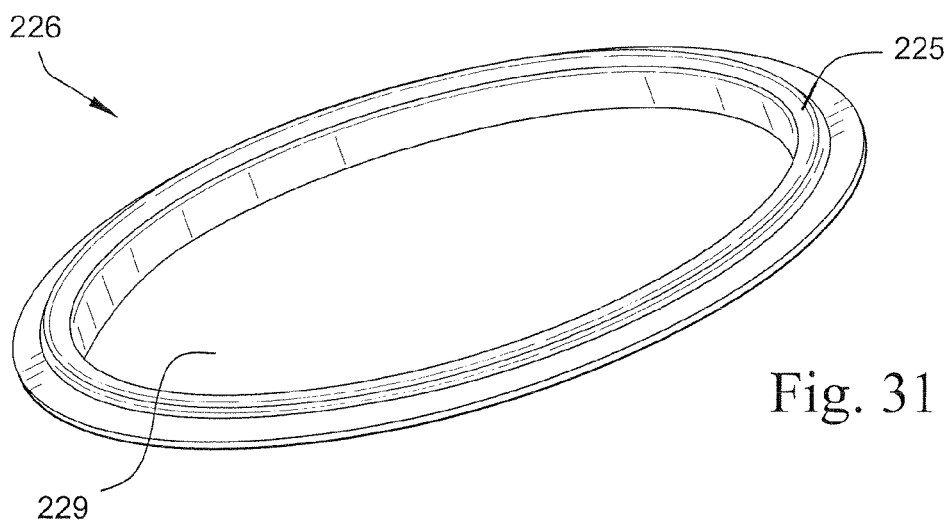
Figure 32:
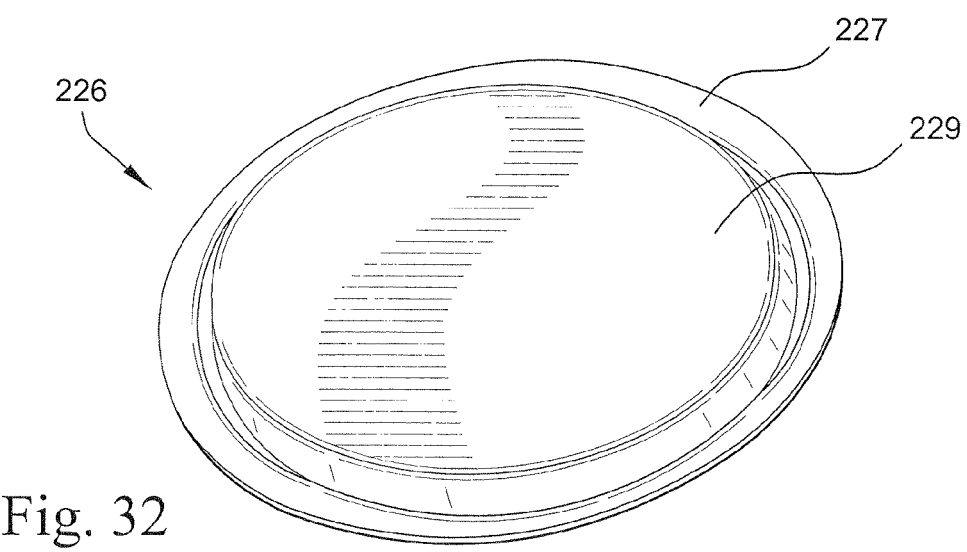

As shown in FIGS. 28-30, the snap ring 250 is connected to the tub base 230, with the base plate 226 in between, by the engagement of snaps 254 formed on the inner periphery of the snap ring 250 that engage snaps 234 formed around the periphery of an opening 232 in the tub base 230. The periphery of the opening 232 of the tub base 230 also includes a plurality of alignment or guide tabs 235 that are received in a channel 255 in the periphery of the snap ring 250. The alignment or guide tabs 235 are received between the snaps 254 of the snap ring 250 when the snap ring 250 is connected to the tub base 230. The alignment or guide tabs 235 thus prevent the snap rings 250 from rotating relative to the tub base 230 and disengagement of the snaps 234, 254.

As shown in FIG. 29, the alignment or guide tabs 235 are provided between the snaps 234 around the periphery of the opening 232. Although eight snaps 234, 254 are shown on the tub base 230 and snap ring 250, respectively, it should be appreciated that any number of snaps may be provided. It should also be appreciated that the opening 232, the snap ring 250 and the base plate 226 may have a shape other than oval, for example circular.

The snap ring 250 retains the base plate 226 to the tub base 230 and prevents the removal of the base plate 226 from the tub base 230. The contact surfaces 252, 227 put pressure on the seal 228 and compress the seal 228 between the snap ring 250 and the base plate 226.

The seal 228 may be a face oriented O-ring. A face oriented O-ring may be used, as the seal is not relied on to retain the base plate 226, which eliminates the effect of friction on the installation of the base plate 226 and retention of the base plate 226. The face oriented O-ring 228 has a shape generally corresponding to the contact surfaces 227, 252 and has a width that is sufficient to permit some misalignment between the tub base 230 and the base plate 226 while still maintaining the substantially waterproof seal. This provides a more reliable and robust seal.

The tub base 230, the base plate 226 and the snap ring 250 are designed to be assembled along a single axis and in one plane. This enables the tub 222 assembly process to be automated, which reduces the cost of manufacture and part-to-part variation.

2.14 Tub Fifteenth Embodiment

Figure 33:
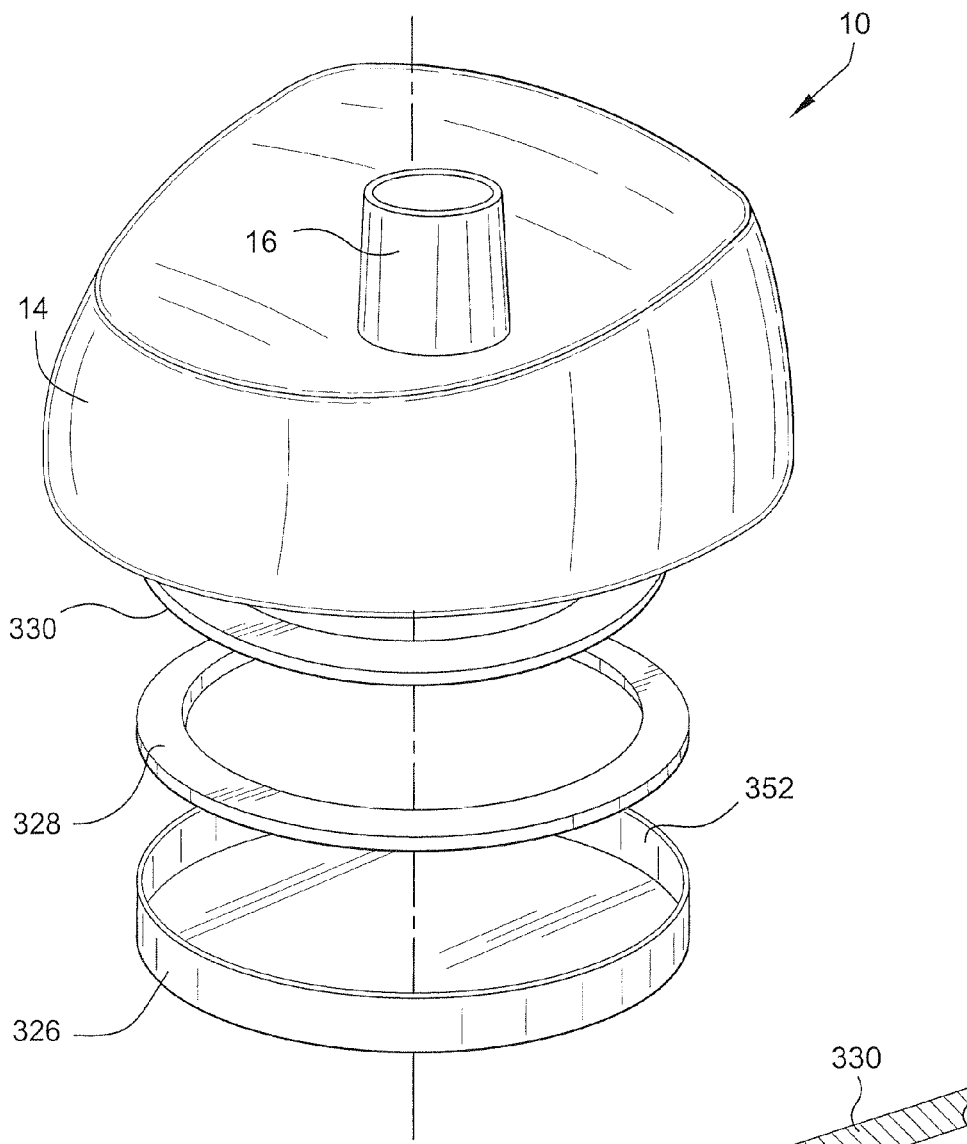
FIGS. 33 and 34 schematically illustrate a humidifier and humidifier tub according to another sample embodiment of the invention.
Figure 34:
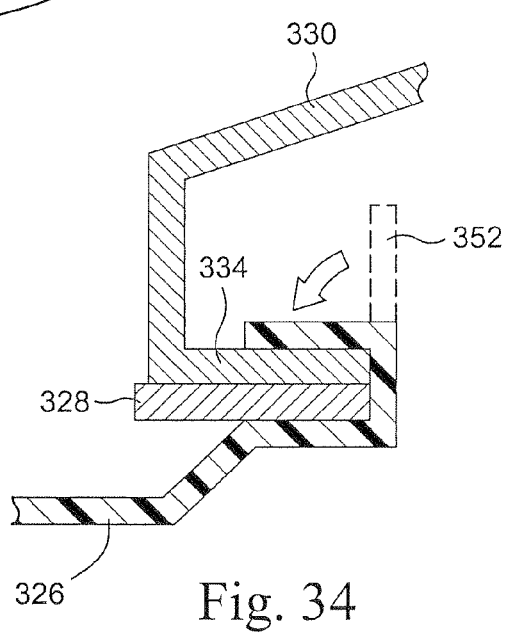

Referring to FIGS. 33 and 34, a humidifier 10 according to another sample embodiment comprises a lid 14 having an outlet 16 configured for connection to a hose or conduit. A tub of the humidifier comprises a tube base 330, a base plate 326 and a seal 328 provided between the tub base 330 and the base plate 326. The base plate 326 comprises a peripheral, e.g. annular, wall 352 that may be folded as shown in FIG. 34 to compress the seal 328 between the base plate 326 and a bottom edge 334 of the tub base 330. The peripheral wall 352 may be folded, for example, by bending the peripheral wall 352, to compress the seal 328 between the bottom edge 334 and the base plate 326. The base plate 326 may be made, for example, for metal, such as stainless steel.

2.15 Tub Sixteenth Embodiment

Figure 35:
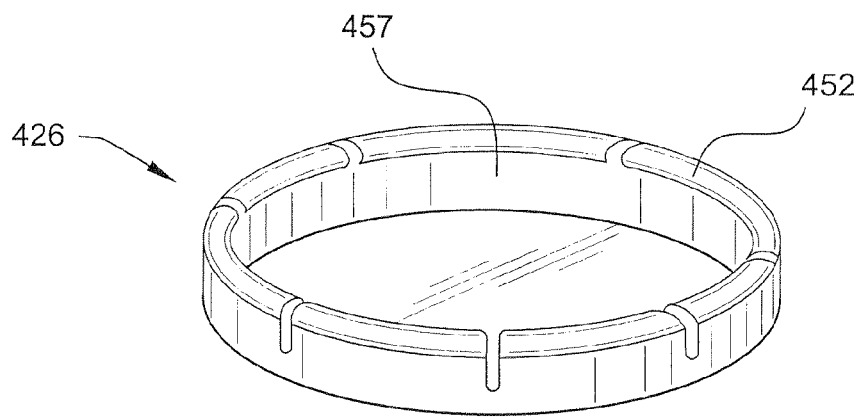
FIGS. 35 and 36 schematically illustrate a humidifier tub according to another sample embodiment of the invention.
Figure 36:
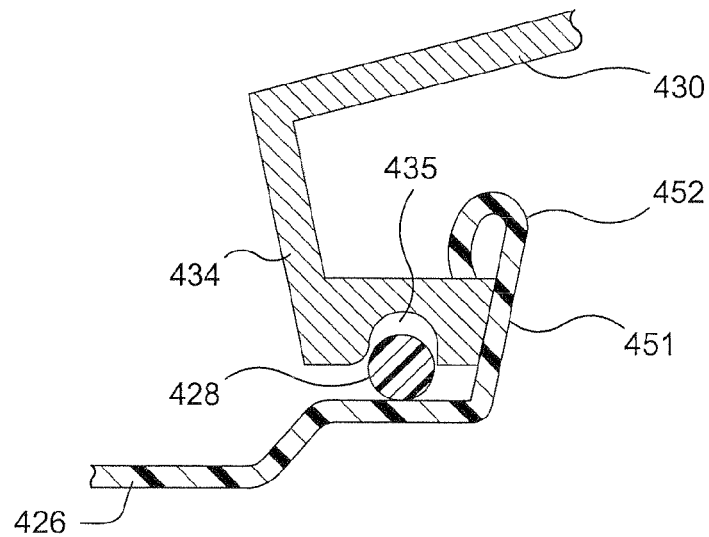

Referring to FIGS. 35 and 36, the base plate 426 of the humidifier tub may comprise an annular wall 451 that includes a curved, or hooked, end 452 that is configured to engage the bottom peripheral edge 434 of the tub base 430. The bottom peripheral edge 434 may include a groove, or channel, 435 configured to accommodate a seal 428, e.g. an O-ring, that is compressed between the base plate 426 and the tub base 430 when the curved end 452 of the base plate 426 engages the bottom peripheral edge 434 of the tub base 430.

2.16 Tub Seventeenth Embodiment

Figure 37:
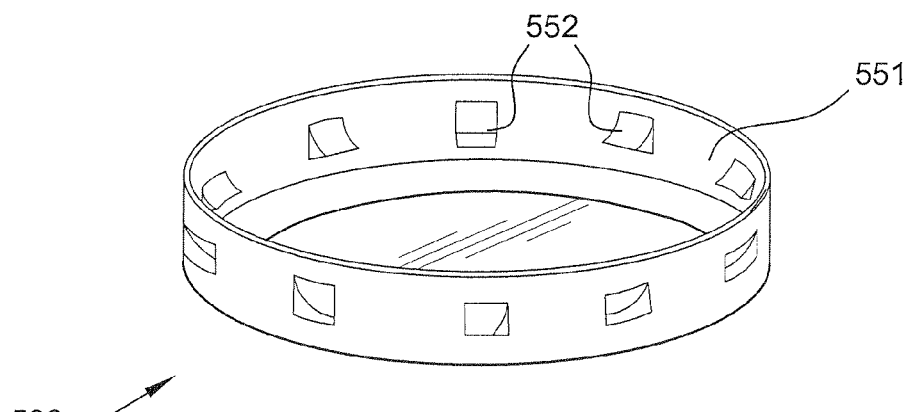
FIGS. 37 and 38 schematically illustrate a humidifier tub according to another sample embodiment of the invention.
Figure 38:
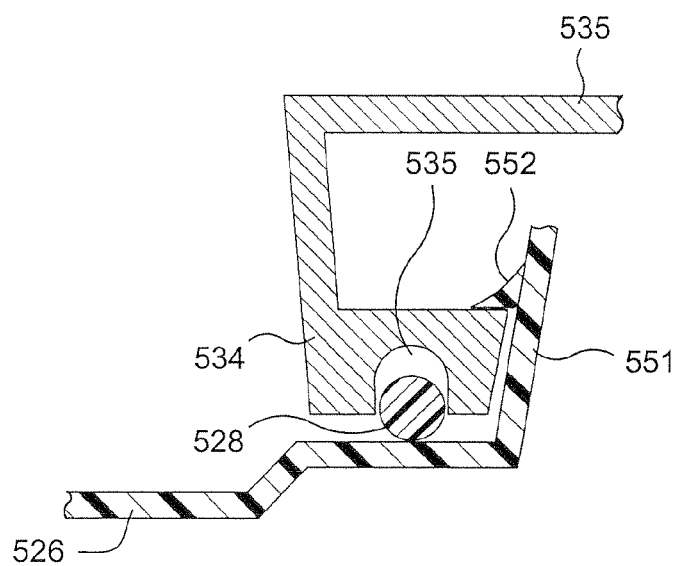

Referring to FIGS. 37 and 38, the base plate 526 of the humidifier tub may comprise an annular wall 551 having a plurality of resilient tabs 552 formed therein. The resilient tabs 552 are configured to engage the bottom peripheral edge 534 of the tub base 530 to compress a seal 528, e.g. an O-ring, between the base plate 526 and the tub base 530. The bottom peripheral edge 534 of the tub base 530 may comprise a groove, or channel, 535 to accommodate the seal 528.

2.17 Tub Eighteenth Embodiment

Figure 39:
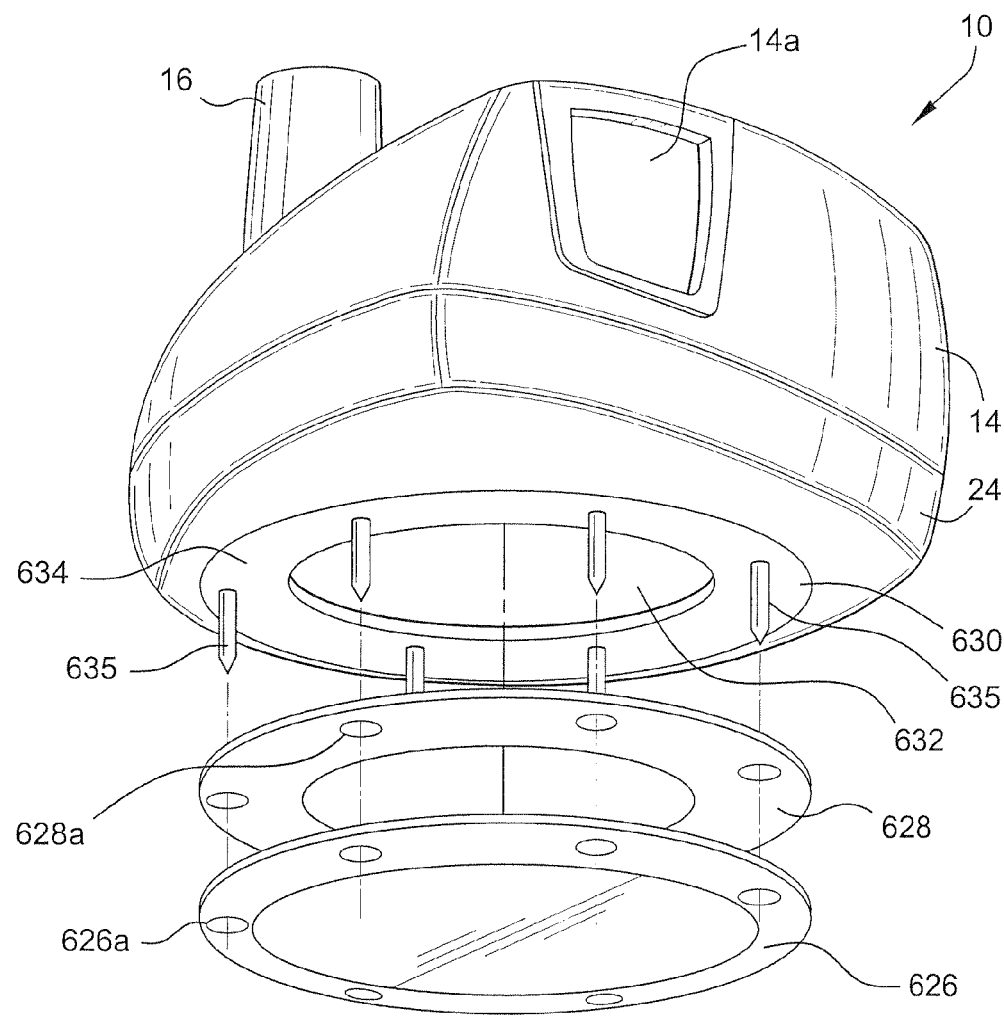
FIG. 39 schematically illustrates a humidifier and humidifier tub according to another sample embodiment of the invention.
Figure 40:
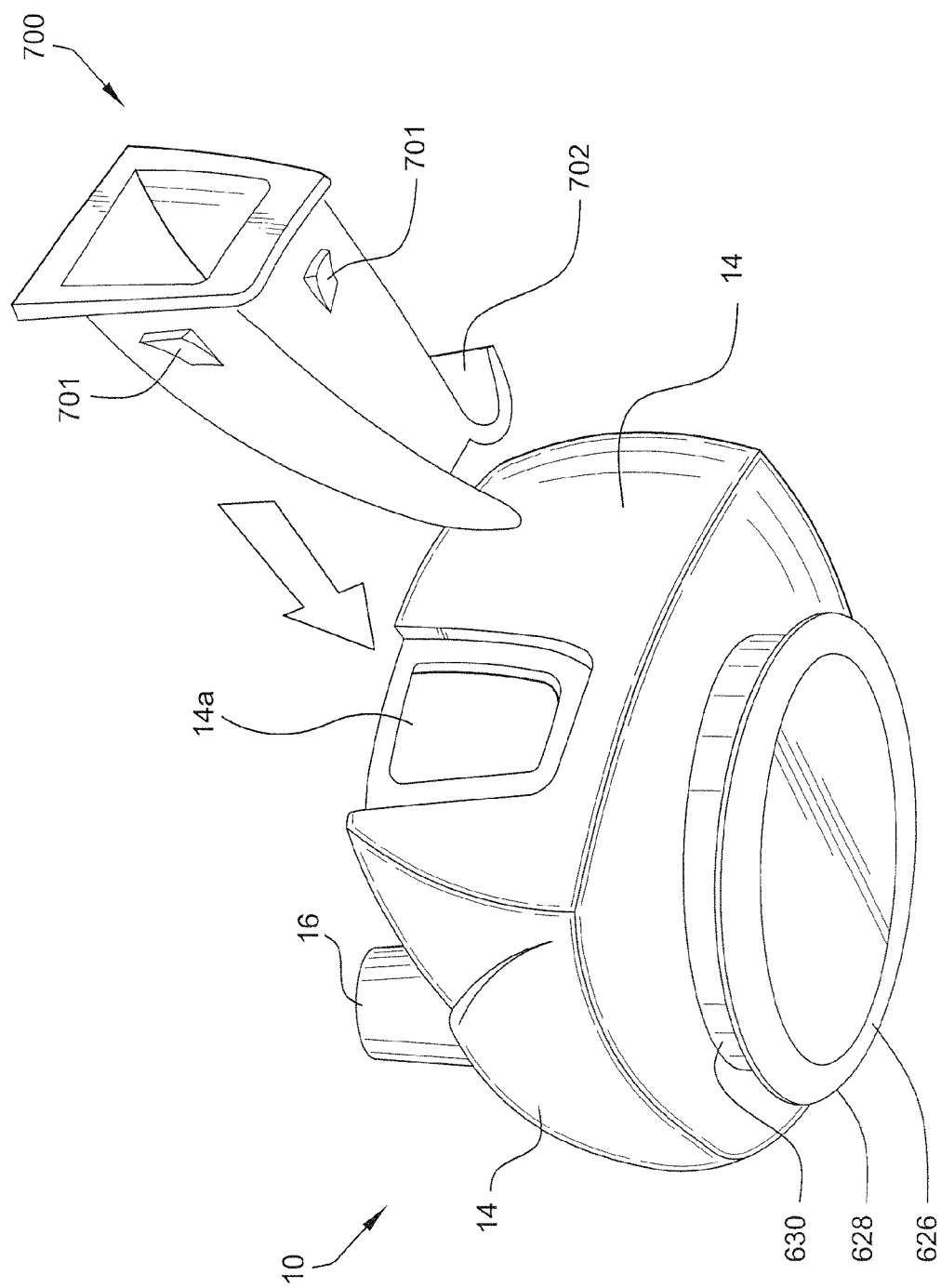
FIG. 40 schematically illustrates a humidifier according to another sample embodiment of the invention.

Referring to FIGS. 39 and 40, a humidifier 10 may comprise a lid 14 having an outlet 16 configured for connection to a hose or conduit. The humidifier may also comprise a water container comprising a tub including a tub lid 24 and a tub. The tub comprises a tube base 630 and a base plate 626. The tub base 630 may comprise an opening 632 surrounded by a bottom peripheral edge 634. The base plate 626 is configured to cover the opening 632 and a seal 628 is provided to seal the connection of the base plate 626 to the tub base 630. The tub base comprises heat stakes 635 that are received in apertures 626a, 628a in the base plate 626 and seal 628, respectively. The ends of the heat stakes 635 are melted, for example by a heated probe or ultrasonically, to form a dome portion similar to the manner described above to permanently connect the base plate 626 to the tube base 630.

As shown in FIG. 40, a cross beam channel 700 is configured for insertion into an inlet 24a of the tub lid 24. The cross beam channel includes flexible tabs that permit insertion of the cross beam channel 700 into the inlet 24a, but prevent removal of the cross beam channel 700 after insertion. The cross beam channel also comprises a curved end 702. The curved end 702 has the dual function of guiding the inlet air over the surface of the water, and to provide spill back protection.

The base plate of the embodiments of the present invention may be formed of a material that provides good heat conduction, for example metal. The base plate may be formed, for example, of stainless steel. As discussed above, the base plate is configured to be in contact with a heating device, such as a ceramic heating pad or plate, to increase the amount of water vapor in the supplied air. A stainless steel base plate transfers more heat to the water in the tub. Increasing the heat transfer from the base plate to the water in the container by using a stainless steel plate also reduces the energy consumption of the humidifier. Transferring more heat to the water in the tub also allows for an increase in the capacity of the tub while maintaining the required level of humidification.

The use of a stamped stainless plate for the base plate also reduces the cost of the humidifier as it is less expensive to provide a stamped plate than a machined plate. To further reduce costs, the tub base may be formed of a plastic material. The tub according to the present invention may also be removed from the humidifier and easily cleaned, for example by placing the tub in a dishwasher.

Although the embodiments described above include seals that are separate from the tub base and the base plate, it should be appreciated that the seal may be formed so as to be integral with the tub base or the base plate, for example by overmolding the seal with the tub base.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A humidifier comprising a water container configured to hold a supply of water, the water container comprising a tub lid coupled to a tub, the tub comprising
   a base plate formed of a heat conducting material;
   a tub base;
   a seal between the base plate and the tub base; and
   a latch mechanism that connects the base plate to the tub base so that the base plate is engaged with the seal, wherein the latch mechanism comprises an overcenter latch pivotably attached to the tub base and latch tabs formed on the base plate, the overcenter latch engaging the latch tabs in a connected position to connect the base plate to the tub base.

2. A humidifier according to claim 1, wherein the overcenter latch comprises a textured surface.

3. A humidifier according to claim 1, wherein the overcenter latch comprises two catches, each catch configured to engage a respective latch tab when the overcenter latch is in the connected position.

4. A humidifier according to claim 3, further comprising two pivot hinges that pivotably connect the overcenter latch to the tub base.

5. A humidifier according to claim 4, wherein each pivot hinge is connected to each catch.

6. A humidifier according to claim 5, wherein each pivot hinge comprises a first pin configured for connection to the tub base and a second pin for connection to the catch.

7. A humidifier according to claim 6, wherein the first pin has larger diameter than the second pin.

8. A humidifier according to claim 1, wherein the base plate is formed of metal.

9. A humidifier according to claim 8, wherein the base plate is formed of stainless steel.

10. A humidifier according to claim 1, wherein the base plate is formed by stamping.

11. A humidifier according to claim 10, wherein the base plate comprises a stamped ring.

12. A humidifier according to claim 11, wherein the stamped ring is circular.

13. A humidifier according to claim 11, wherein the stamped ring is D-shaped.

14. A humidifier according to claim 1, wherein the base plate comprises upturned edges.

15. A humidifier according to claim 1, wherein the base plate comprises alignment tabs and the tub base includes alignment slots configured to receive the alignment tabs.

16. A humidifier according to claim 15, wherein the alignment tabs are spaced apart by about 5 mm-15 mm.

17. A humidifier according to claim 16, wherein the alignment tabs are spaced apart by about 10 mm.

18. A humidifier according to claim 15, wherein the alignment tabs and the latch mechanism provide a generally triangular compression region for the seal.

19. A humidifier according to claim 1, wherein the seal is provided in a groove formed in the tub base.

20. A humidifier according to claim 19, wherein the seal comprises an O-ring.

21. A humidifier according to claim 1, wherein the seal is overmolded to the tub base.

22. A humidifier according to claim 1, wherein the tub base comprises ribs at a connection between the latch mechanism and the base plate.

23. A humidifier according to claim 22, wherein the tub base further comprises a gap provided between at least two of the ribs.

24. A humidifier according to claim 1, wherein the tub lid is configured to cover the tub, and the tub lid comprises an air inlet aperture configured to receive a flow of air from a flow generator connectable to the humidifier, an air passage configured to deliver the flow of air to the tub, and an outlet configured to pass humidified air out of the tub.

25. A humidifier according to claim 24, further comprising a cradle configured to receive the water container.

26. A humidifier according to claim 25, wherein the cradle is configured to be connected to the flow generator.

27. A humidifier according to claim 25, wherein the cradle comprises a hinged lid, the hinged lid being pivotable between an open position permitting insertion of the water container into the cradle and a closed position covering the inserted water container.

28. A humidifier according to claim 27, wherein the hinged lid comprises an air outlet pipe configured to communicate with the outlet of the tub lid when the hinged lid is the closed position.

29. A humidifier according to claim 25, wherein the cradle comprises a heating element configured to contact the base plate when the water container is inserted into the cradle.

30. A CPAP device comprising a humidifier according to claim 1.

31. A humidifier comprising a tub configured to hold a supply of water, the tub comprising
a tub base forming a bottom portion of the tub;
a base plate at least partly sealed against and positioned at a bottom portion of the tub base; and
a latch mechanism adapted to sealingly connect the base plate to the tub base, wherein the latch mechanism comprises an overcenter latch pivotably attached to the tub base and latch tabs formed on the base plate, the overcenter latch engaging the latch tabs in a connected position to connect the base plate to the tub base.

32. A humidifier according to claim 31, wherein the base plate is detachable from the tub base when the overcenter latch is disengaged from the latch tabs, and the base plate is secured to the tub base when the overcenter latch is engaged with the latch tabs.

* * * * *